US008252547B2

(12) United States Patent
Mikoshiba et al.

(10) Patent No.: US 8,252,547 B2
(45) Date of Patent: Aug. 28, 2012

(54) IN VITRO CONTROL OF PROTEIN SYNTHESIS IN MAMMALIAN CELLS BY IP3 RECEPTOR-BINDING PROTEIN

(75) Inventors: Katsuhiko Mikoshiba, Tokyo (JP); Hideaki Ando, Tokyo (JP); Akihiro Mizutani, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 443 days.

(21) Appl. No.: 12/293,681

(22) PCT Filed: Mar. 20, 2007

(86) PCT No.: PCT/JP2007/056529
§ 371 (c)(1),
(2), (4) Date: Sep. 19, 2008

(87) PCT Pub. No.: WO2007/108557
PCT Pub. Date: Sep. 27, 2007

(65) Prior Publication Data
US 2010/0167314 A1    Jul. 1, 2010

(30) Foreign Application Priority Data
Mar. 20, 2006 (JP) ................................ 2006-077607

(51) Int. Cl.
A61K 38/00    (2006.01)
A61K 31/7088  (2006.01)
C07K 14/47    (2006.01)
C12Q 1/02     (2006.01)
G01N 33/15    (2006.01)

(52) U.S. Cl. .......... 435/7.8; 435/455; 530/300; 514/1.1; 536/23.5

(58) Field of Classification Search ........................ None
See application file for complete search history.

(56) References Cited

U.S. PATENT DOCUMENTS
2005/0181450 A1    8/2005    Mikoshiba

FOREIGN PATENT DOCUMENTS
| EP | 1 408 049 A2 | 4/2004 |
| JP | 2004-129612 A | 4/2004 |
| WO | WO 03/055997 A1 | 7/2003 |
| WO | WO/2004/030615 * | 4/2004 |
| WO | WO 2004/030615 A2 | 4/2004 |
| WO | WO 2004/041170 A2 | 5/2004 |

OTHER PUBLICATIONS

Patel et al. Molecular properties of inositol 1,4,5-triphosphate receptors. Cell Calcium 25:247-264, 1999.*
Skolnick et al. From genes to protein structure and function: novel applications of computational approaches in the genomic era. Trends in Biotechnology 18:34-39, 2000.*
Schwarze et al., In Vivo Protein Transduction: Delivery of a Biologically Active Protein into the Mouse, Science, 285, 1569-1572, 1999.*
Howell et al., Deoxyribonuclease II is a Lysosomal Barrier to Transfection, Mol. Therapy, 8, 957-963, 2003.*
Mittal V., Improving the efficiency of RNA interference in mammals, Nature Reviews, 5, 355-365, 2004.*
Hideomi Yamada et al., "IRBIT wa pNBC1 no Makuhatsugen o Sokushin suru", The Japanese Journal of Nephrology, 2005, vol. 47, No. 3, p. 288 "P-300".
Eiten Gross et al., "Structural determinants and significance of regulation of electrogenic Na+—HCO3 cotransporter stoichiometry", Am. J. Physiol. Renal. Physiol. 283: F879-F887, 2002.
Kyoko Shirakabe et al., "IRBIT, an inositol 1,4,5-trisphosphate receptor-binding protein, specifically binds to and activates pancreas-type NA+/HCO3 contransporter 1 (pNBC1)", PNAS, vol. 103, No. 25, Jun. 20, 2006, pp. 9542-9547.
Benoit Devogelaere et al., "Binding of IRBIT to the IP3 Receptor: Determinants and Functional Effects", Biochemical & Biophysical Research Communications 343 (2006) 49-56.
Hideaki Ando et al., "IRBIT, a Novel Inositol 1,4,5-Trisphosphate (IP3) Receptor-binding Protein is Released from IP3 Receptor upon IP3 Binding to the Receptor", The Journal of Biological Chemistry, vol. 278, No. 12, Issue of Mar. 21, pp. 10602-10612, 2003.
Supplementary European Search Report EP 07739967.3 dated Sep. 30, 2009.
European Search Report EP 10 19 1552 dated Mar. 16, 2011.
European Search Report EP 10 19 1554—dated Mar. 16, 2011.
Katja A. Lamia et al., "Increased Insulin Sensitivity and Reduced Adiposity in Phosphatidylinositol 5-Phosphate 4-Kinase β−/−Mice", Molecular and Cellular Biology, Jun. 2004, vol. 24, No. 11, pp. 5080-5087.
Michael J. Berridge et al., "The Versatility and Universality of Calcium Signalling", Nature Reviews, Molecular Cell Biology, vol. 1, Oct. 2000, pp. 11-21.
Michael J. Berridge, "Inositol triphosphate and calcium signalling", Nature, vol. 361, Jan. 28, 1993, pp. 315-325.
Olivier Blondel et al., "Sequence and Functional Characterization of a Third Inositol Trisphosphate Receptor Subtype, IP3R-3, Expressed in Pancreatic Islets, Kidney, Gastrointestinal Tract, and Other Tissues", The Journal of Biological Chemistry, vol. 268, No. 15, Issue of May 25, 1993, pp. 11356-11363.
Paul F. Worley et al., "Inositol trisphosphate receptor localization in brain: variable stoichiometry with protein kinase C", Nature, vol. 325, Jan. 8, 1987, pp. 159-161.
Teiichi Furuichi et al., "Inositol 1,4,5-Trisphosphate Receptor-Mediated $Ca^{2+}$Signaling in the Brain", Journal of Neurochemistry, vol. 64, No. 3, 1995, pp. 953-960.
Teiichi Furuichi et al., "Primary structure and functional expression of the inositol 1,4,5-trisphosphate-binding protein $P_{400}$", Nature, vol. 342, No. 6245, Nov. 2, 1989, pp. 32-38.
Teiichi Furuichi et al., "Widespread Expression of Inositol 1,4,5-Trisphosphate Receptor Type 1 Gene (Insp3r1) in the Mouse Central Nervous System", Receptors and Channels, vol. 1, 1993, pp. 11-24.
Thomas C. Sudhof et al., "Structure of a novel $InsP_3$receptor", The EMBO Journal vol. 10, No. 11, pp. 3199-3206, 1991.

* cited by examiner

*Primary Examiner* — Elly-Gerald Stoica
(74) *Attorney, Agent, or Firm* — Stephen A. Bent; Foley & Lardner LLP

(57) ABSTRACT

The present invention provides a composition comprising an $IP_3$ receptor-binding protein (IRBIT), a nucleic acid that controls the expression and translation of IRBIT, or an antibody against IRBIT for controlling at least one intracellular biological function selected from the group consisting of (1) protein synthesis, (2) phosphatidylinositol metabolism, and (3) intracellular pH.

5 Claims, 15 Drawing Sheets
(1 of 15 Drawing Sheet(s) Filed in Color)

Fig. 4
A
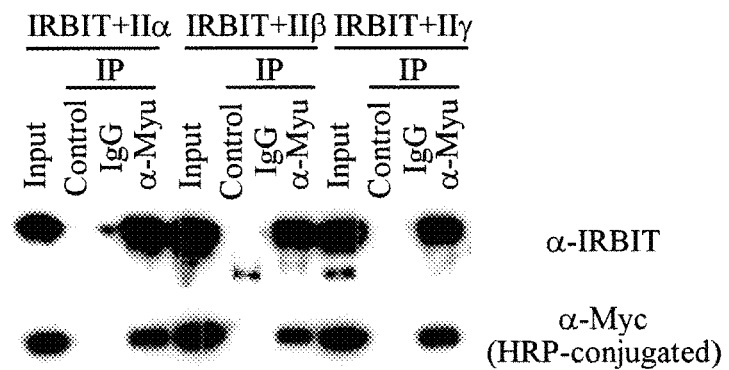
B
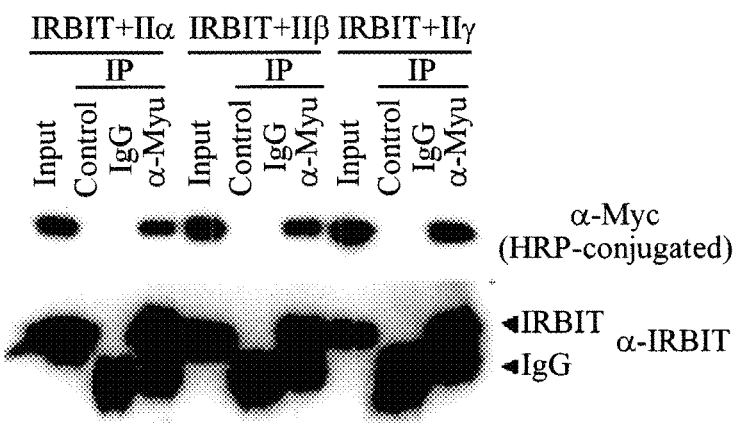

Fig. 9
A
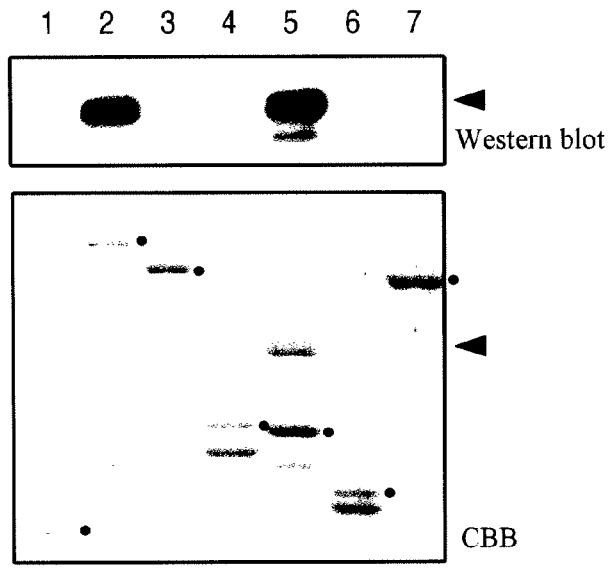
B
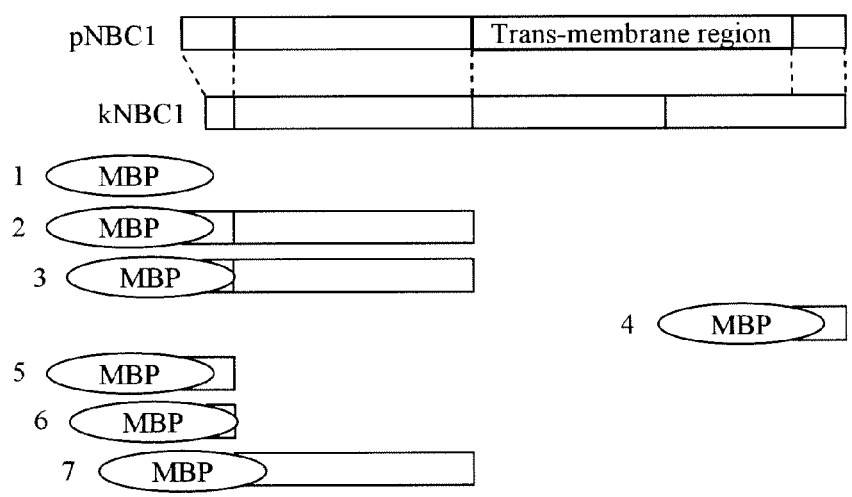

Fig. 10
A
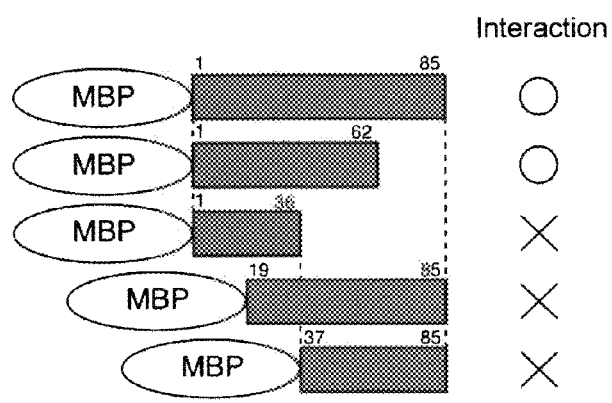
B
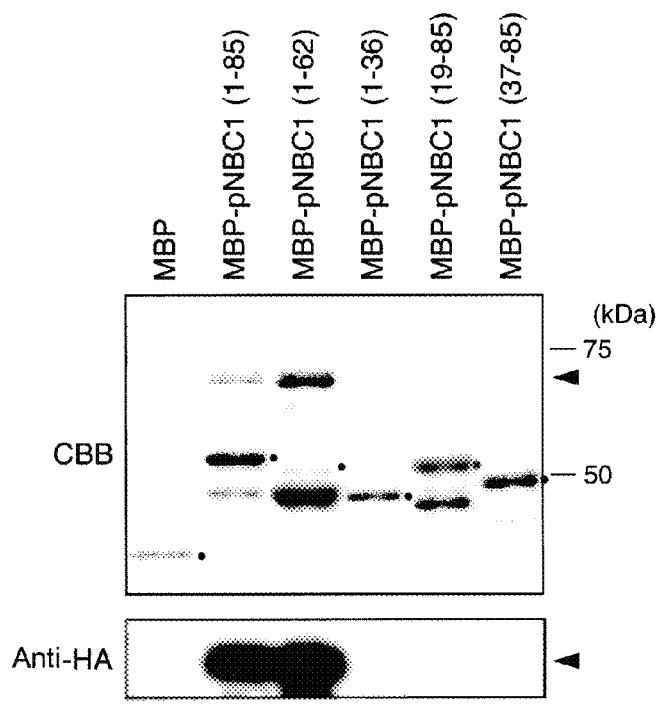

Fig. 11
A
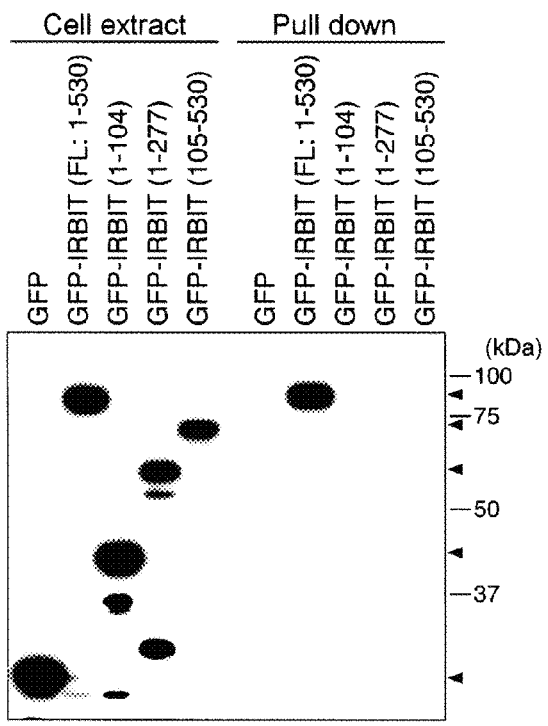
B
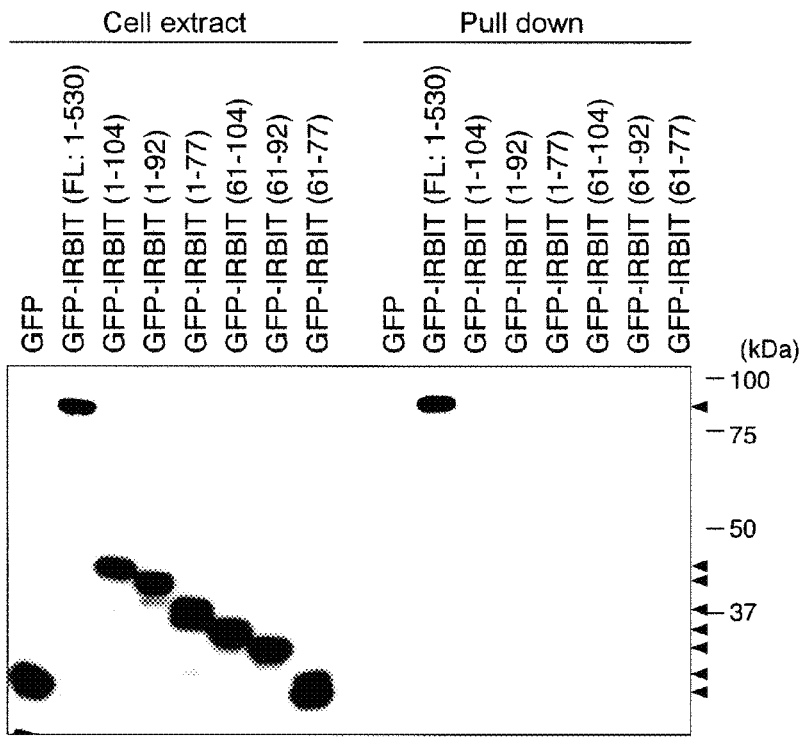

Fig. 14
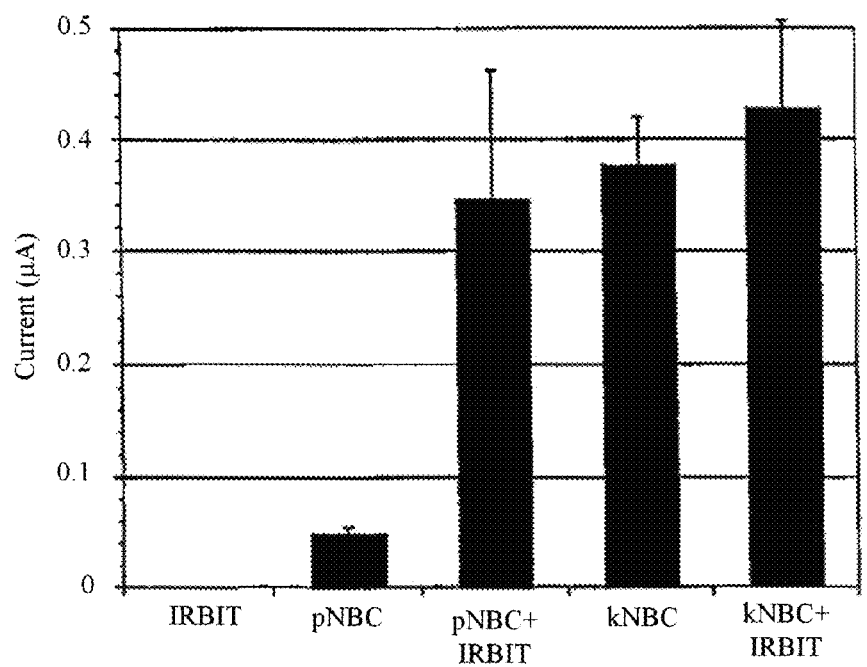
A
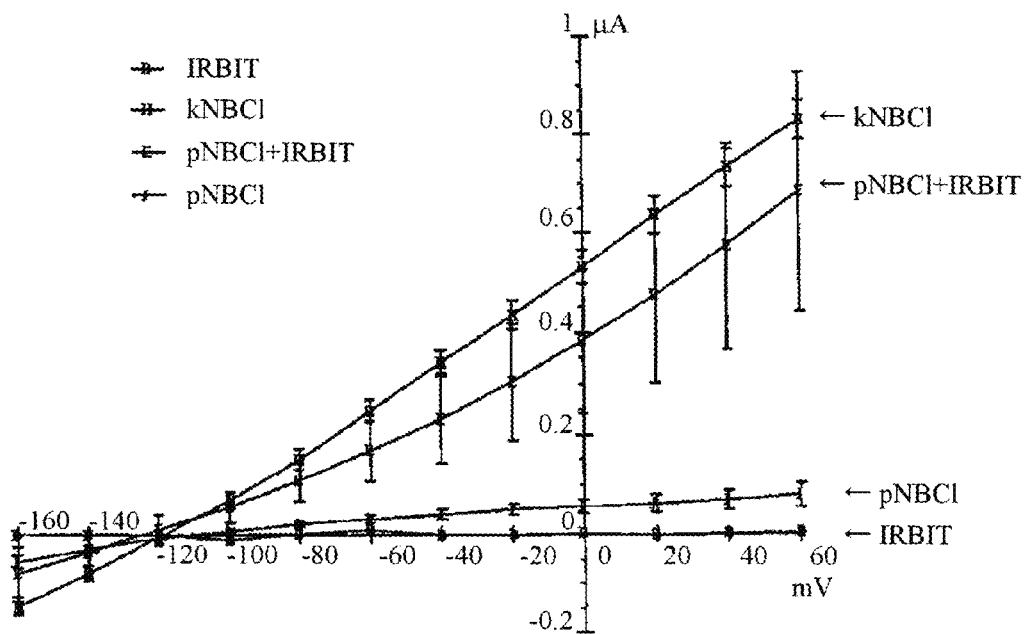
B

IN VITRO CONTROL OF PROTEIN SYNTHESIS IN MAMMALIAN CELLS BY IP3 RECEPTOR-BINDING PROTEIN

TECHNICAL FIELD

The present invention relates to compositions and methods for controlling biological functions in mammalian cells. More specifically, the present invention relates to compositions and methods for controlling the biological functions in which an $IP_3$ receptor-binding protein (IRBIT) and its intracellular target molecules are involved.

The present invention further provides a method for screening for a substance with the use of such control of biological functions.

BACKGROUND OF THE INVENTION

When phosphatidylinositol 4,5-bisphosphate is hydrolyzed through the activation of a receptor on a cell membrane, inositol 1,4,5-trisphosphate ($IP_3$), which is an intracellular second messenger, is generated. $IP_3$ binds to an $IP_3$ receptor ($IP_3R$), thereby inducing $Ca^{2+}$ release from organelles for intracellular calcium storage (mainly, the endoplasmic reticulum). In this $IP_3/Ca^{2+}$ signaling pathway, the $IP_3$ receptor plays a role in converting the $IP_3$ signal into $Ca^{2+}$ signal (M. J. Berridge, Nature (1993) 361: 315-325; M. J. Berridge et al., Nat. Rev. Mol. Cell. Biol. (2000) 1: 11-21; T. Furuichi and K. Mikoshiba, J. Neurochem. (1995) 64: 953-960).

The $IP_3$ receptor is a tetrameric intracellular $IP_3$-gated $Ca^{2+}$ release channel. In mammals, there exist 3 different types of $IP_3$ receptors (i.e., type 1, type 2, and type 3) (T. Furuichi et al., Nature (1989) 342: 32-38; T. Sudhof et al., EMBO J. (1991) 10: 3199-3206; O. Blondel et al., J. Biol. Chem. (1993) 268: 11356-11363). Of them, the type 1 $IP_3$ receptor ($IP_3R1$) is expressed at high levels in the central nervous system and particularly in the cerebellum (P. F. Worley et al., Nature (1987) 325: 159-161; T. Furuichi et al., Recept. Channels (1993) 1: 11-24). Mouse $IP_3R1$ comprises 2749 amino acids and has 3 functionally different regions. Specifically, an $IP_3$-binding domain is present in the vicinity of the N-terminus, a channel-forming domain having a six-transmembrane region is present in the vicinity of the C terminus, and a control region is present between the two regions. The deletion mutant analysis of the $IP_3$-binding domain revealed that the amino acids 226-578 of the $IP_3$ receptor was a minimum region required for specific and high-affinity binding of a ligand. This region is referred to as the $IP_3$ binding core.

With an increase of cytoplasmic $Ca^{2+}$ concentration by activation of the $IP_3$ receptor, the activities of a wide variety of downstream target molecules are controlled. These downstream target molecules play important roles in wide-ranging cellular responses including fertilization, development, proliferation, secretion, synaptic plasticity, and the like.

The present inventors have previously discovered a novel $IP_3$ receptor-binding protein and named it "IRBIT" ($IP_3R$-binding protein released with inositol 1,4,5-trisphosphate) (JP2004-129612A). The $IP_3$ receptor is widely distributed in various tissues and cells of mammals such as humans and mice (e.g., in the brain, heart, liver, kidney, pancreas, and thymus gland). Accordingly, IRBIT is inferred to be present also in such tissues or cells. The amino acid and nucleotide sequences of mouse IRBIT have been determined by the present inventors (JP2004-129612A, H. Ando et al., J. Biol. Chem. (2003) 278: 10602-10612). Such IRBIT comprises 530 amino acids. Human IRBIT and mouse IRBIT share 100% identity. The region for binding to the $IP_3$ receptor is present in the N-terminal region of IRBIT, corresponding to amino acids 1-104 in a human or a mouse.

IRBIT is characterized in that: (1) IRBIT is a neutral protein (presumed pI: 6.48) in which the N-terminal region is relatively acidic (presumed pI: 4.98); (2) a plurality of phosphorylation sites are localized in a concentrated manner in the N-terminal region, so that phosphorylation is predicted to be necessary for interaction with $IP_3R1$; (3) the lysine residue at position 508, which is essential for the binding of $IP_3R1$ to $IP_3$, is also essential for interaction with IRBIT; (4) IRBIT is dissociated by $IP_3$ from interaction with $IP_3R1$; and (5) because IRBIT is dissociated from $IP_3R1$ and is extracted from crude microsome fractions by high salt, it is inferred that its interaction with $IP_3R1$ takes place due to electrostatic binding, for example (JP2004-129612A).

IRBIT has the property that it binds to the $IP_3$ binding region of the $IP_3$ receptor and is dissociated in vitro from the $IP_3$ receptor by $IP_3$. Therefore, it has also been revealed that IRBIT has a function of suppressing the activity of the $IP_3$ receptor by suppressing the binding of $IP_3$ to the $IP_3$ receptor (JP2004-129612A).

The present inventors have now found target molecules of IRBIT and important biological in vivo functions of IRBT as a tertiary messenger, as described below.

DISCLOSURE OF THE INVENTION

An object of the present invention is to provide a composition and a method that make it possible to control intracellular biological functions with the use of interaction between IRBIT and its molecular targets.

Another object of the present invention is to provide a method for screening for a substance that makes it possible to control the above biological functions by suppressing or enhancing the binding between IRBIT and its molecular targets within cells.

This time, the present inventors have conducted concentrated studies to achieve the above objects. The present inventors have thus found that targets of IRBIT are a molecule which controls a protein synthesis, a molecule which controls phosphatidylinositol, and a molecule which controls a pH within cells. Moreover, the present inventors have now proved that IRBIT has a role as a tertiary messenger (particularly, as an important molecule for controlling intracellular metabolism) for controlling the functions of binding to the 3 types of target molecules discovered in connection therewith, thereby controlling the functions of the target molecules.

SUMMARY OF THE INVENTION

The present invention, in summary, has the following characteristics.

In the first aspect, the present invention provides a composition comprising an $IP_3$ receptor-binding protein (IRBIT), a nucleic acid which controls the expression and translation of IRBIT, or an antibody against IRBIT, wherein the composition is for controlling at least one intracellular biological function selected from the group consisting of:
(1) protein synthesis;
(2) phosphatidylinositol metabolism; and
(3) intracellular pH.

In one embodiment, cytoplasmic mRNA polyadenylation mediated by a cleavage/polyadenylation specificity factor (CPSF) is involved in the above-mentioned protein synthesis.

In another embodiment, intracellular $PIP_2$ synthetase (PIP-KII) is involved in the above-mentioned phosphatidylinositol metabolism.

In another embodiment, intracellular p-type Na/HCO₃ cotransporter 1 (pNBC1) is involved in the above-mentioned intracellular pH.

In another embodiment, the control is suppression or elevation.

In another embodiment, the IRBIT is derived from a human or a mouse.

In another embodiment, the IRBIT is a protein comprising an amino acid sequence shown in SEQ ID NO: 1 or SEQ ID NO: 3 or a protein which comprises an amino acid sequence having 90% or more identity with said amino acid sequence and has a biological activity equivalent to that of IRBIT.

In another embodiment, the above composition is used in vivo, in vitro, or ex vivo.

In another embodiment, the above composition is for treatment of diseases.

In the second aspect, the present invention also provides use of IRBIT in in vitro or ex vivo control of the synthesis of protein within cells.

In an embodiment thereof, the IRBIT binds to CPSF to control a function of CPSF.

In the third aspect, the present invention further provides use of IRBIT in in vitro or ex vivo control of the metabolism of phosphatidylinositol within cells.

In an embodiment thereof, the IRBIT suppresses PIPKII activity.

In the fourth aspect, the present invention further provides use of IRBIT in in vitro or ex vivo control of a pH within cells.

In an embodiment thereof, the IRBIT activates pNBC1.

In another embodiment, activation of the pNBC1 requires phosphorylation of the IRBIT.

In the fifth aspect, the present invention further provides a method for screening for a substance, comprising measuring a binding of IRBIT with CPSF, PIPKII, or pNBC1 in the presence of a candidate substance and then identifying a substance that suppresses or elevates said binding.

In an embodiment thereof, the substance is for treatment or diagnosis.

In another embodiment, the binding is performed within a mammalian cell.

In still another embodiment, the substance controls at least one intracellular biological function selected from the group consisting of intracellular protein synthesis, phosphatidylinositol metabolism, and intracellular pH.

DEFINITIONS

The term "IRBIT" as used herein refers to an IP₃ receptor-binding protein derived from a mammal, which binds to an IP₃ binding site of the IP₃ receptor and is released into cytoplasm when IP₃ binds to the receptor. In the present invention, IRBIT binds to CPSF (cleavage/polyadenylation specificity factor), PIPKII (phosphatidylinositol-5-phosphate 4-kinase), or pNBC1 (pancreas-type Na/HCO₃ cotransporter 1). These IRBIT targeting proteins exert important biological functions, which are involved in the protein synthesis, phosphatidylinositol metabolism, and intracellular pH maintenance respectively, through their bindings to IRBIT within cells. Thus, the IRBIT is responsible for controlling each of the biological functions.

The term "protein synthesis" as used herein refers to a series of intracellular gene transcription and translation processes. In the present invention, the control of mRNA polyadenylation in cytoplasm is involved in the protein synthesis. Moreover, the term "phosphatidylinositol metabolism" refers to the metabolism of phospholipids including IP₃.

The term "suppression" as used herein refers to decrease, reduction, or inhibition of the above-mentioned biological functions.

The term "elevation" as used herein refers to increase, rise, or enhancement of the above-mentioned biological functions.

The term "ex vivo" as used herein refers to a case in which cells or tissue removed from a living body are treated with the composition of the present invention and then returned into the living body.

The term "patient" as used herein refers to a mammal such as human, mouse, rat, dog, cat, or domestic animal (e.g., cattle, horse, pig, sheep, or goat), preferably human.

This specification includes all or part of the contents as disclosed in the description and/or drawings of Japanese Patent Application No. 2006-77607, to which the present application claims priority.

BRIEF DESCRIPTION OF THE DRAWINGS

The application contains at least one drawing executed in color. Copies of this patent or patent application publication with color drawing(s) will be provided by the Office upon request and payment of the necessary fee.

In FIG. 1, "I.B." denotes Western blotting, "I.P." denotes immunoprecipitation, "HA" denotes hemagglutinin as a tag, and "load" denotes a cell extract.

In FIG. 3, "PLC" denotes phospholipase C.

FIG. 4 shows the binding of mouse IRBIT to Myc-PIPKIIα, β, and γ. FIG. 4A shows immunoprecipitation with an anti-Myc antibody. FIG. 4B shows immunoprecipitation with an anti-IRBIT antibody. In FIG. 4, "Input" denotes a cell extract, "IP" denotes immunoprecipitation, "Control IgG (negative control)" denotes a sample subjected to immunoprecipitation using the control IgG.

FIG. 7A is a schematic diagram of IRBIT deletion mutants. FIG. 7B shows the binding of deletion mutants obtained by deletion from an N-terminal side of IRBIT, to Myc-PIPKIIα. FIG. 7C shows the binding of deletion mutants obtained by deletion from the C-terminal side of IRBIT, to Myc-PIPKIIα.

In FIG. 8, "Input" denotes a cell extract, "IP" denotes immunoprecipitation, and "IB" denotes Western blotting.

FIG. 9A shows the results of Western blotting (top panel) showing the binding of IRBIT and NBC1. IRBIT (black triangle (◄)) binds to only recombinant proteins 2 and 5 containing portions specific to pNBC1 (pancreas-type). In the SDS polyacrylamide gel electrophoretic image (bottom panel of FIG. 9A), each recombinant protein (1, 2, 3, 4, 5, 6, or 7) is denoted with a black circle (●). Furthermore, FIG. 9B schematically shows the structures of these recombinant proteins in addition to the structures of pNBC1 and kNBC1 (kidney-type). In FIG. 9, "MBP" denotes a maltose-binding protein tag used for purification and "CBB" denotes coomassie brilliant blue.

FIG. 10 shows the ability of binding between NBC1 deletion mutants and IRBIT. FIG. 10A shows the results of causing expression of pNBC1 deletion mutants separately in *Escherichia coli*, purifying the resultants, and then examining the binding (or interaction) with HA-IRBIT (where "HA" denotes hemagglutinin) forcedly expressed in COS7 cells via pull down assay. Furthermore, the top panel in FIG. 10B shows the results of subjecting pulled down samples to SDS-PAGE and then staining the samples with CBB. The bottom panel in FIG. 10B shows the results of subjecting pulled down samples to Western blotting using an anti-HA antibody. Black triangles (◄) indicate electrophoretic movilities of HA-IRBIT and black dots (•) indicate the electrophoretic movilities of deletion mutant proteins.

FIG. 11 shows the ability of binding between IRBIT deletion mutants and pNBC1. Each type of IRBIT deletion mutant was forcedly expressed in COS7 cells in the form of fusion protein fused with GFP (green fluorescent protein) and then the binding to pNBC1 was examined via pull down assay. Both FIG. 11A and FIG. 11B show the results of subjecting cell extracts (Lysate) or pulled down samples (Pull down) each expressing a deletion mutant to SDS-PAGE and then to Western blotting using an anti-GFP antibody. Black triangle (◄) indicates an electrophoretic movility of each deletion mutant. It was understood that all IRBITs other than the full-length (FL) had become unable to bind to pNBC1.

FIG. 14 shows the activation of pNBC1 by IRBIT, as measured by a voltage-clamp method. FIG. 14A shows current values (μA) obtained when the membrane potential was fixed at −25 mV. Furthermore, FIG. 14B shows I-V curves that represent current changes when the membrane potential was varied between −160 mV and +60 mV.

PREFERRED EMBODIMENTS OF THE INVENTION

Hereinafter, the present invention will be described in more detail.
1. Composition
According to the $1^{st}$ aspect, the present invention provides a composition comprising IRBIT, a nucleic acid controlling the expression and translation of IRBIT, and an antibody against IRBIT. The composition of the present invention is used for controlling at least one intracellular biological function selected from the group consisting of (1) protein synthesis, (2) phosphatidylinositol metabolism, and (3) intracellular pH.

Control of the above three biological functions will be described as follows.
Control of Protein Synthesis In the present invention, the above control of protein synthesis is the control of mRNA polyadenylation mediated by intracellular binding of IRBIT with CPSF.

Figure 1:
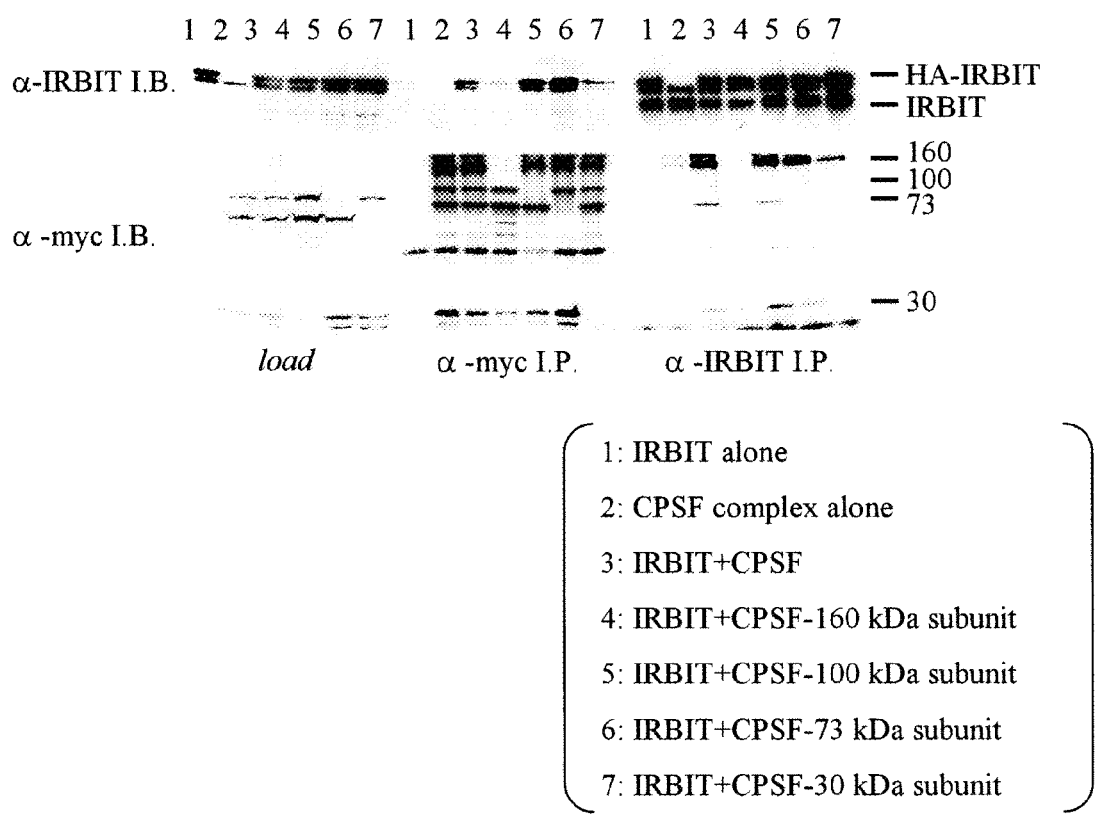
FIG. 1 shows the results of Western blotting showing the binding of IRBIT to CPSF160.

CPSF is a conjugated protein consisting of four subunits, CPSF160, CPSF100, CPSF73, and CPSF30. The present inventors have discovered this time that IRBIT binds to CPSF and particularly binds to CPSF160 as a result of coprecipitation tests involving coexpression in COS cells and immunoprecipitation (FIG. 1).

CPSF is a molecule essential for intranuclear mRNA polyadenylation reactions and is also known to have a function of regulating protein synthesis via extension of poly(A) length in the cytoplasm. Furthermore, the mRNA binding site of CPSF160 is known to be essential for CPSF to recognize mRNA to which poly(A) is added, for example (C. Barnard Daron et al., Cell 2004, 119: 641-651, and E. Klann et al., "Synaptic Plasticity and Translation Initiation," Learning & Memory 2004, 11: 365-372, Cold Spring Harbor Laboratory Press). Specifically, a section in "Cytoplasmic polyadenylation and CPEB" (E. Klann et al., (mentioned above), pp. 367 to 368) discloses that: polyadenylation is regulated by two sequences in the 3' non-translated region of mRNA; that is, cytoplasmic polyadenylation element (CPE) and AAUAAA; CPE binding protein (CPEB), which is an important regulatory protein of polyadenylation, is phosphorylated by specific protein kinase (Aurora); such kinase phosphorylates CPEB, so that CPSF interacts with CPEB on the AAUAAA sequence, poly(A) polymerase (PAP) is recruited, and a poly(A) tail portion of mRNA is extended.

Figure 2:
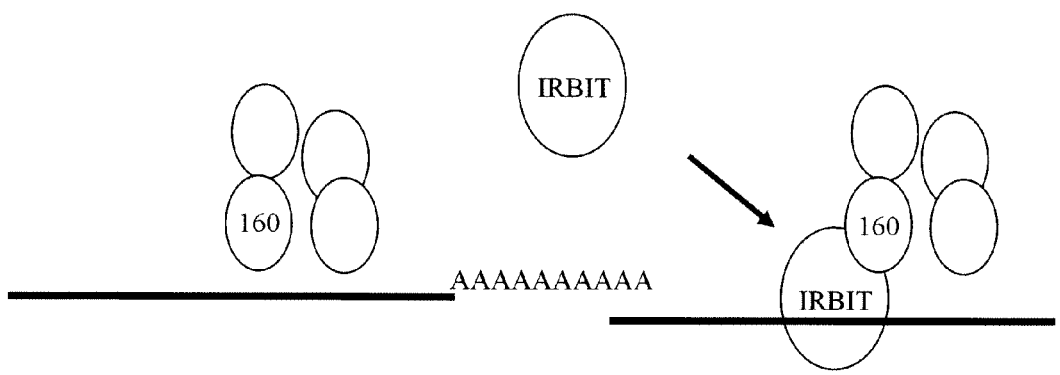
FIG. 2 is a schematic diagram showing that IRBIT binds to an mRNA binding site of a CPSF160 subunit of CPSF.

In view of the above findings, it is considered that IRBIT binds to the mRNA binding site of CPSF160, so that CPSF functions are controlled (FIG. 2).

Furthermore, the present inventors have obtained this time a finding that IRBIT has a function of further suppressing polyadenylation activity (I. Kaufmann et al., EMBO J. (2004) 23: 616-626) in the presence of PAP and Fip1 (CPSF subunit). Based on the finding, the suppression of protein synthesis is made possible by IRBIT.

As described above, IRBIT is involved in control of mRNA polyadenylation and thus involved in control of protein synthesis through its binding to CPSF.

Therefore, IRBIT, or a substance that suppresses or enhances the generation and functions of IRBIT, makes it possible to control CPSF-associated protein synthesis.
Control of Phosphatidylinositol Metabolism IRBIT further binds to PIPKII, so as to suppress the activity of the enzyme (Example 2).

PIPKII is an enzyme for synthesis of phosphatidylinositol 4,5-diphosphate (PI (4,5) $P_2$) from phosphatidylinositol pentaphosphate (PI (5) P). Furthermore, $IP_3$ is produced via hydrolysis of $PIP_2$. $IP_3$ is a ligand of an $IP_3$ receptor. $IP_3$ binds to the receptor so that calcium ion ($Ca^{2+}$) and IRBIT are together released within the cytoplasm. When the fact is taken into consideration, it can be said that IRBIT is involved in control of phosphatidylinositol metabolism (Katja A. Lamia et al., Mol. Cell. Biol. 2004, 24: 5080-5087).

Figure 3:
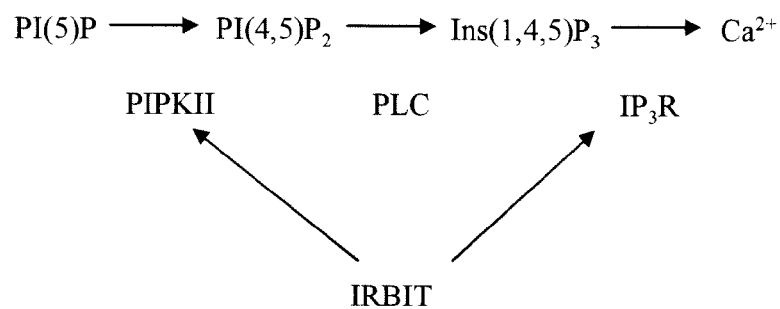
FIG. 3 is a schematic diagram showing the phosphatidylinositol metabolism in which an IP₃ receptor, IRBIT, PIPKII, and IP₃ are involved.

Therefore, IRBIT, or a substance that suppresses or enhances the generation and functions of IRBIT, makes it possible to control PIPKII-associated phosphatidylinositol metabolism (FIG. 3).

For example, PIPKII contains 3 types of isoform including PIPKIIα, β, and γ in mammals, and IRBIT binds to all of these enzymes. Particularly with regard to PIPKIIβ, it has been demonstrated that inhibition of the enzyme is useful for treatment of type 2 diabetes (Katja A. Lamia et al., ibid) based on the fact that a transgenic mouse with a knocked-out gene corresponding to the enzyme has high insulin sensitivity. The finding of the present inventors that IRBIT suppresses PIPKII activity suggests that IRBIT can be used for treatment of type 2 diabetes.

Control of Intracellular pH

IRBIT further binds to pNBC1, so as to activate pNBC1.

Specifically, IRBIT cRNA and NBC1 cRNA were injected into *Xenopus* oocytes. The degree of pNBC1 response detected in connection with intracellular pH change was approximately 6 to 7 times higher than the degree detected before pH change (FIG. 14). This result demonstrates that IRBIT significantly enhances pNBC1 activity.

NBC1 is a 10-transmembrane protein existing on the cell membrane and functions to transport sodium ions and bicarbonates at a constant rate in the same direction across the cell membrane. In vivo pH is cleverly regulated by balancing between bicarbonate concentration and carbon dioxide gas concentration. Thus, it is considered that NBC1 is involved in regulation of in vivo pH (E. Gross and I. Kurtz, Am. J. Physiol. Renal Physiol. 2002, 283: F876-F887). In particular, identification of NBC1 as a causative gene of proximal renal tubular acidosis, which is a type of acidaemia due to which blood pH approaches acidic levels suggests that the transport of bicarbonates by NBC1 plays a role essential for in vivo pH maintenance.

Concerning NBC1, two splicing mutants have been reported: a kidney-type (kidney-type: kNBC1) and a pancreas-type (pancreas-type: pNBC1). kNBC1 is mainly expressed in the kidney and pNBC1 is mainly expressed in the pancreas and in relatively many tissues including the cerebral nervous system. To reveal to which one of NBC1s and to which part of NBC1 the IRBIT binds, the present inventors have caused the expression of the cytoplasmic region of NBC1 as a recombinant protein in *Excherichia coli*, purified the recombinant protein, and then examined the binding of the protein with IRBIT forcedly expressed in cultured cells by pull down assay. As a result, it was revealed that IRBIT specifically and strongly binds to pNBC1-specific N-terminal 85 amino acids (FIG. 10). Furthermore, it was also revealed that the binding between IRBIT and pNBC1 is controlled by changes in specific salt concentration.

These results strongly suggest the possibility that IRBIT controls pH regulation mediated by pNBC1 in various organs in a manner depending on intracellular conditions. Moreover, patients with proximal renal tubular acidosis develop eye diseases such as glaucoma and cataract or present various symptoms including dwarfism, mental retardation, pancreatitis, and the like. pH regulation conducted by NBC1 is considered to also play an important role in organs other than the kidney. Therefore, IRBIT is also useful through mediation of pNBC1 for methods for treating eye diseases such as glaucoma and cataract and diseases such as dwarfism, mental retardation, and pancreatitis (Seth L. Alper, Annu. Rev. Physiol. 2002, 64: 899-923).

Therefore, IRBIT, or a substance that suppresses or enhances the generation or functions of IRBIT, makes it possible to control pNBC1-associated intracellular pH.

$IP_3$ Receptor-Binding Protein (IRBIT)

IRBIT to be used in the present invention is derived from a mammal. IRBIT is known to be present in the intracellular endoplasmic reticulum of tissues such as the brain, heart, liver, kidney, pancreas, and thymus gland of a mammal (JP2004-129612 A). Preferable examples of IRBIT include human IRBIT and mouse IRBIT (JP2004-129612 A, H. Ando et al., J. Biol. Chem. 2003, 278: 10602-10612). Particularly, human IRBIT is preferable. The amino acid and nucleotide sequences of human IRBIT and mouse IRBIT are deposited with the GenBank under NM_006621 (see SEQ ID NOS: 1 and 2) and NM_145542 (see SEQ ID NOS: 3 and 4), respectively.

Furthermore, another preferable example of IRBIT is a protein comprising an amino acid sequence having 90% or more, preferably 95% or more, more preferably 98% or more, and most preferably 99% or more identity with the amino acid sequence shown in SEQ ID NO: 1 or SEQ ID NO: 3 and having biological activity equivalent to that of IRBIT. As used herein, the term "biological activity" refers to, in addition to S-adenosylhomocysteine hydrolase-like activity that catalyzes reversible hydrolysis of S-adenosylhomocysteine into adenosine and homocysteine, activity involved in control of biological functions including the control of mRNA polyadenylation that is mediated via binding with CPSF in protein synthesis, the control of phosphatidylinositol metabolism that is mediated via binding with PIPKII, and the control of intracellular pH that is mediated via binding with pNBC1.

Similarly, a preferable example of DNA encoding IRBIT is DNA having 90% or more, preferably 95% or more, more preferably 98% or more, and most preferably 99% or more identity with the nucleotide sequence shown in SEQ ID NO: 2 or SEQ ID NO: 4, or, DNA capable of hybridizing under stringent conditions to the nucleotide sequence of SEQ ID NO: 2 or SEQ ID NO: 4. Here, the stringent conditions consist of, but are not limited to, hybridization at approximately 45-50° C. in 2-6×SSC (sodium chloride/sodium citrate), followed by washing at approximately 50-65° C. with 0.2-2× SSC/0.1-1% SDS, or hybridization at 60-65° C. in 6×SSC, Denhard't solution, and 0.2% SDS, followed by washing at 60-65° C. with 0.2×SSC and 0.1% SDS (e.g., F. M. Ausbel et al., Short Protocols in Molecular Biology ($3^{rd}$ edition) A Compendium of Methods from Current Protocols in Molecular Biology, 1995, John Wiley & Sons, Inc.).

IRBITs derived from other mammals can also be used in the present invention. Examples of such IRBITs include IRBIT derived from an experimental animal such as a rat, a hamster, and a rabbit, IRBIT derived from a pet animal such as a dog and a cat, and IRBIT derived from a domestic animal such as cattle, a horse, a pig, sheep, and a goat. These IRBITs are prepared as follows. Probes and/or primers are prepared based on an amino acid or nucleotide sequence described in a document, databank, or the like or based on a known sequence of human or mouse IRBIT. IRBIT cDNA is cloned and/or amplified by a commonly employed technique such as a DNA cloning method or polymerase chain reaction (PCR) using a commercial library or a library constructed from the prepared animal tissues, for example. Furthermore, the thus obtained DNA encoding IRBIT is incorporated into a commercial expression vector (e.g., plasmid) having an appropriate regulatory sequence, for example. The expression vector is transformed into appropriate host cells or host cells are transfected with the expression vector. The thus obtained cells are cultured in appropriate medium, so as to cause expression of IRBIT DNA. The thus generated IRBIT protein can be collected. A series of these techniques are described in, for example, J. Sambrook et al., Molecular Cloning A Laboratory Manual, 1989, Cold Spring Harbor Laboratory Press, F. M. Ausbel et al., Short Protocols in Molecular Biology (3$^{rd}$ edition) A Compendium of Methods from Current Protocols in Molecular Biology, 1995, John Wiley & Sons, Inc., Experimental Medicine, Separate Volume, 4$^{th}$ edition, Edited by Masami Matsumura et al., "New Genetic Engineering Handbook" (2003) YODOSHA, Tokyo, Japan, and the like. IRBIT homologs derived from various mammals can be obtained according to such techniques described in these documents.

A mammalian tissue containing an IRBIT gene is homogenized using a homogenizer and then centrifuged at approximately 10,000 rpm, so that a supernatant is obtained. Subsequently, total RNA is collected by a guanidine.acidic phenol method, for example, cDNA is synthesized according to a standard method, and then DNA encoding IRBIT can be obtained from the cDNA. For example, ISOGEN (trademark) of NIPPON GENE is commercially available as a kit for RNA extraction and can also be used herein.

The size of a probe for detection of DNA encoding IRBIT is generally 30 or more nucleotides and preferably 50 to 100 or more nucleotides. In general, a label such as a fluorescent label (e.g., fluorescamine, rhodamine, or their derivatives thereof), a radioactive isotope label (e.g., $^{32}$P), or the like is bound to a probe. Thus, the binding of DNA encoding target IRBIT with the probe can be detected.

The size of a primer for amplification of DNA encoding IRBIT generally ranges from 15 to 30 nucleotides and preferably ranges from 20 to 25 nucleotides. Primers to be used herein should have sequences complementary to the 3' terminal sequences of the sense strand and the antisense strand of DNA encoding IRBIT. However, when the sequence of IRBIT-encoding DNA to be amplified is unknown, a plurality of primers are prepared based on known IRBIT sequences, a template DNA is amplified by PCR, and then formal primers are prepared based on the thus amplified template DNA, so that target template DNA can be amplified by PCR.

PCR is generally performed by performing approximately 20 to 40 cycles each consisting of DNA denaturation, primer annealing, and elongation reaction. DNA denaturation is a step for separating double-stranded DNA into single-chain DNAs, which is performed by approximately 15 seconds to 1 minute of treatment generally at 94° C. Primer annealing is a step for annealing a primer to complementary single-chain template DNA. The optimum temperature or time for annealing depends on the nucleotide sequence of a primer or the length thereof. In general, annealing treatment is performed at approximately 55-60° C. for approximately 30 seconds to 1 minute. Elongation reaction is a step for elongation of template DNA in the presence of 4 types of dNTP and heat-resistant DNA polymerase. In general, elongation reaction is performed at 72° C. for approximately 30 seconds to 10 minutes. Before the initiation of the cycles, DNA can be completely denatured by heating at 94° C. for approximately 1 to 5 minutes. Furthermore, after completion of the entire cycles, approximately 1 to 5 minutes of heat treatment can also be performed at 72° C. Heat-resistant DNA polymerase is commercially available and Thermus aquatics (Taq) polymerase (marketed by TaKaRa, PerkinElmer, Pharmacia, or the like) can be used, for example. Concerning PCR techniques, Protein, Nucleic Acid, and Enzyme "Frontiers of PCR from Basic Technology to Application," vol. 41, No. 5, Apr. 1996, Extra Number, KYORITSU SHUPPAN, Tokyo, Japan can be referred, for example.

An expression vector to be used herein may be any vector that can be used in prokaryote- or eukaryote-derived cells. A vector can contain regulatory sequences such as a promoter, a replication origin, a ribosome-binding site, a multicloning site, and a terminator. As expression vectors, plasmid or viral vectors, or the like, and particularly commercially-available vectors such as pGEX-4T-1 (Amersham Pharmacia Biotech), pBluescript II SK, pHS19, pHS15, pG-1, and pXT1 (Stratagene Corporation), pMAL and pTYB series (Daiichi Pure Chemicals), pQE series (Qiagen), pET series (Novagen), pSVK3 and pSVL SV40 (Pharmacia), pcDNA1 and pcDM8 (Funakoshi), and pHB6, pVB6, pHM6, pVM6, and pXM (Roche Diagnostics) can be adequately selected and used.

Examples of host cells include bacteria of the genus *Escherichia*, such as *Escherichia coli*, bacteria of the genus *Bacillus*, such as *Bacillus subtilis*, and bacteria of the genus *Pseudomonas*, bacteria of the genus *Corynebacterium*, yeasts such as yeast of the genus *Saccharomyces*, yeast of the genus *Pichia*, and yeast of the genus *Schizosaccharomyces*, insect cells, plant cells, and mammalian cells (e.g., CHO, COS, and HEK293 cells).

Examples of a method for introducing DNA encoding IRBIT into host cells include a calcium phosphate method, a lipofection method, an electroporation method, and a method using infection with viruses such as adenovirus or retrovirus (Experimental Medicine, Separate Volume, 4$^{th}$ Edition, Edited by Masami Matsumura et al., "New Genetic Engineering Handbook (2003) YODOSHA, Tokyo, Japan).

More specifically, concerning mouse IRBIT, IRBIT purification from mature mouse cerebellum and cDNA cloning and expression are disclosed in JP2004-129612 A. The disclosure is available for reference.

The biological activity of IRBIT can be determined based on an analogous assay method since IRBIT has homology with S-adenosylhomocysteine hydrolase that catalyzes reversible hydrolysis of S-adenosylhomocysteine into adenosine and homocysteine. This assay method can be performed according to the method of C. S. Yuan et al., (J. Biol. Chem. 1996, 271: 28009-28016), for example. This is briefly explained as follows. This assay method comprises performing the above hydrolysis reaction using IRBIT (approximately 3 µg) and rabbit S-adenosylhomocysteine hydrolase (Sigma) (approximately 2.5 µg), causing the thus generated product (homocysteine) to react with 5,5'-dithiobis (2-nitrobenzoate) (Sigma), measuring the thus obtained color at 412 nm using a spectrophotometer, and then finding the absorbance.

Nucleic Acid Controlling IRBIT Expression and Translation

In the present invention, examples of nucleic acids that control IRBIT expression and translation include DNA encoding IRBIT, antisense RNA of mRNA encoding IRBIT or a fragment thereof, ribozyme that makes it possible to cleave mRNA encoding IRBIT, functional RNA such as siRNA (small interfering RNA), and vector DNA containing such DNA or RNA (actually, DNA encoding RNA).

DNA encoding IRBIT is derived from a mammal such as a human or a mouse and can be prepared by a technique as explained in the above section, "IP$_3$ receptor-binding protein (IRBIT)." Preferable DNA encoding IRBIT is DNA comprising the nucleotide sequence that encodes the amino acid sequence shown in SEQ ID NO: 1 or SEQ ID NO: 3. More preferable DNA is DNA comprising the nucleotide sequence shown in SEQ ID NO: 2 or SEQ ID NO: 4 and encoding human or mouse IRBIT.

DNA encoding IRBIT is inserted into an expression vector (e.g., a plasmid or viral vector) and thus can be used for the intracellular expression of IRBIT.

A plasmid vector for expression of DNA encoding IRBIT can contain, in addition to a DNA sequence encoding IRBIT and a promoter, regulatory sequences such as a drug resistance gene (e.g., a neomycin resistance gene, an ampicillin resistance gene, a puromycin resistance gene, and a hygromycin resistance gene), a terminator, a multiple cloning site, a replication origin, and a ribosome-binding site.

As a viral vector for expression of DNA encoding IRBIT, an adenoviral vector, an adeno-associated viral vector, a lentiviral vector, a retroviral vector (e.g., leukemia viral vector), a herpes viral vector, or the like can be used, for example. A preferable type of a viral vector is deficient in replication competence, for example, so as not to cause disease when the vector is applied to a human. For example, in the case of an adenoviral vector, a replication competence-deficient adenoviral vector (e.g., pAdeno-X (Invitrogen)) prepared by deletion of E1 and E3 genes can be used. A method described in the document can be used for construction of such a viral vector (e.g., U.S. Pat. No. 5,252,479 and International Publication WO94/13788).

As a promoter, a promoter that enables expression of foreign DNA within mammalian cells can be used. Examples of such promoter include a cytomegalovirus (CMV) promoter, a SV40 promoter, and an EF promoter.

In the case of a plasmid vector, a complex of such a plasmid vector with positively charged liposome such as Lipofectamine, Lipofectin, CellFECTIN, or positively charged cholesterol is formed, the complex is capsulated, and then the resultant can be introduced into a living patient's body (e.g., Mamoru Nakanishi et al., Protein, Nucleic Acid, and Enzyme, Vol. 44, No. 11, pp. 48-54, 1999, KYORITSU SHUPPAN, Tokyo, Japan; Clinical Cancer research 59: 4325-4333, 1999; Wu et al., J. Biol. Chem. 1987, 262: 4429). Furthermore, in the case of a viral vector, such a viral vector is introduced into an affected part for infecting cells, so that gene transfer into cells can be performed (L. Zender et al., Proc. Natl. Acad. Sci. U.S.A. (2003), 100: 77797-7802; H. Xia et al., Nature Biotech. (2002), 20: 1006-1010; X. F. Qin et al., Proc. Natl. Acad. Sci. U.S.A. (2003), 100: 183-188; G. M. Barton et al., Proc. Natl. Acad., Sci. U.S.A. (2002), 99: 14943-14945; J. D. Hommel et al., Nature Med. (2003), 9: 1539-1544). In particular, it has been confirmed that gene transfer can be performed with very high efficiencies into various cell species with the use of an adenoviral vector or an adeno-associated viral vector. Such vectors are not incorporated into the genome, so that their effects are exerted temporarily and the safety of such vectors is thought to be much higher than other viral vectors.

Moreover, antisense RNA of mRNA encoding IRBIT or a fragment thereof can inhibit the translation of an IRBIT gene to an IRBIT protein.

The above fragment can comprise a sequence consisting of the number of nucleotides, which is approximately continuous 30 or more nucleotides, 50 or more nucleotides, 70 or more nucleotides, 100 or more nucleotides, 150 or more nucleotides, 200 or more nucleotides, or 250 or more nucleotides, but is the same or less than the full-length sequence of an IRBIT gene or mRNA.

Antisense RNA or a fragment thereof may comprise halogen (fluorine, chlorine, bromine or iodine) and a modification group such as a methyl, carboxymethyl, or thio group.

The above antisense nucleic acid can be synthesized using a known DNA/RNA synthesis technique or a DNA recombination technique. When such antisense nucleic acid is synthesized by a DNA recombination technique, polymerase chain reaction (PCR) is performed using vector DNA containing the nucleotide sequence of IRBIT as a template and primers that sandwich a sequence to be amplified, so as to amplify the target sequence. If necessary, the product is cloned into a vector, and then antisense DNA can be generated. Alternatively, DNA having the thus obtained amplified target sequence is inserted into a vector, and then the vector is introduced into eukaryotic or prokaryotic cells, so that antisense RNA can be obtained with the use of the transcription system.

Similar inhibition can also be performed using ribozyme that enables cleavage of mRNA encoding IRBIT or functional RNA such as siRNA.

siRNA can contain a sense strand sequence (derived from mRNA sequence that is encoded by the nucleotide sequence of SEQ ID NO: 2 (human IRBIT) or SEQ ID NO: 4 (mouse IRBIT), for example) with a length of approximately continuous 18 to 30, preferably approximately 19 to 25, and further preferably approximately 20 to 23 nucleotides and a complementary sequence thereof that is an antisense strand sequence. Here, the term "sense strand sequence" refers to the same nucleotide sequence as that of a target site of the above mRNA. Furthermore, the term "antisense strand sequence" refers to a nucleotide sequence complementary to the sense strand sequence. A sense strand and antisense strand can anneal together to form double-stranded siRNA. siRNA can further comprise an overhang (e.g., UU) consisting of 1 to 5 nucleotides at each 3' end of sense and antisense strands.

For selection of a sense strand sequence of siRNA, known understandings for selection of a target site of target IRBIT mRNA can be employed. For example, criteria that can be employed are: that (a) GC content ranges from approximately 30% to 70% and is preferably approximately 50%, (b) all nucleotides are equal and G is discontinuous, (c) the 5' terminal nucleotides of an antisense strand are A and U (D. M. Dykxhoorn et al., Nature Rev. Mol. Cell. Biol. (2003), 77: 7174-7181; A. Khvorova et al., Cell (2003), 115: 209-216). Furthermore, a candidate gene site on IRBIT mRNA that is a target site of the above siRNA can be inferred using the mfold RNA secondary structure prediction program (J. A. Jaeger et al., Methods in Enzymology 1989, 183: 281-306; D. H. Mathews et al., J. Mol. Biol. 1999, 288: 911-940). For example, a sequence that siRNA can target can be determined by inferring based on the above findings and then actually confirming the effects. Examples of siRNA that can be used in the present invention include, but are not limited to, the following sequences.

```
IRBIT siRNA-1:
AAAUCCAGUUUGCUGAUGACA      (SEQ ID NO: 5)

IRBIT siRNA-2:
AACUCAGAAUGAAGUAGCUGC      (SEQ ID NO: 6)
``` siRNA can be synthesized using a known chemical synthesis technique. For example, siRNA can be obtained via chemical synthesis using a conventionally used DNA/RNA autosynthesizer or by commissioning the synthesis thereof to a company handling the synthesis of siRNA and the like (e.g., Funakoshi (Tokyo, Japan), Dharmacon, or Ambion).

When siRNA is introduced into cells or tissues, siRNA is directly injected into cells or tissues or a vector that enables siRNA expression is preferably used. Alternatively, a complex is formed using siRNA or a vector and liposome such as Lipofectamine, Lipofectin, CellFECTIN, or another positively-charged liposome (e.g., positively charged cholesterol) or a microcapsule and then the complex can also be used (e.g., Mamoru Nakanishi et al., Protein, Nucleic Acid, and Enzyme, Vol. 44, No. 11, pp. 48-54, 1999, KYORITSU SHUPPAN, Tokyo, Japan; Clinical Cancer research 59: 4325-4333, 1999; Wu et al., J. Biol. Chem. 1987, 262: 4429).

A vector for expression of siRNA contains a DNA sequence encoding siRNA or a precursor thereof under regulation of a promoter.

An example of an expression vector is a hairpin vector. This type of vector contains DNA encoding hairpin RNA in which the above sense strand RNA sequence and the above antisense strand RNA sequence are covalently bound via a single-chain loop sequence, wherein the DNA is a vector such that the hairpin RNA is formed via intracellular transcription and then the hairpin RNA is processed by a dicer to form the above siRNA. A poly T sequence comprising 1 to 6 and preferably 1 to 5 Ts is ligated to the 3' end of hairpin DNA encoding siRNA as a transcription termination signal sequence or for overhanging. It is desired that short hairpin RNA (shRNA) as an siRNA precursor transcribed from vector DNA have an overhang comprising 2 to 4 Us at the 3' end of the antisense strand. Because of the presence of such overhang, sense strand RNA and antisense strand RNA can increase their stability against degradation by nuclease. One endogenous dicer is present in a human and is responsible for converting long-chain dsRNA or precursor micro RNA (miRNA) into siRNA and mature miRNA, respectively. Examples of a promoter include a pol III promoter such as human- or mouse-derived U6 promoter, and an H1 promoter, a pol II promoter, and a cytomegalovirus promoter.

Another example of an expression vector is a tandem vector. This vector contains a DNA sequence encoding a sense strand RNA sequence that composes the above siRNA and a DNA sequence encoding an antisense strand RNA sequence consecutively. The vector further contains DNA in which a promoter is ligated to the 5' end of each strand and a poly T sequence is ligated to the 3' end of each strand, wherein the DNA is a vector such that the sense strand RNA and the antisense strand RNA hybridize to each other after intracellular transcription, so as to form the above siRNA.

An example of a promoter for such tandem vector is a pol III promoter such as a human- or a mouse-derived U6 promoter or an H1 promoter, or a cytomegalovirus promoter. Furthermore, a poly T sequence is a poly T sequence comprising 1 to 6 and preferably 1 to 5 Ts. Such a tandem vector is introduced into cells and then transcribed into RNAs corresponding to a sense strand and an antisense strand. The strands hybridize to each other, so that a target siRNA can be generated.

The above hairpin and tandem vectors are plasmid vectors or viral vectors. A plasmid vector can be prepared using techniques described in the following Examples or methods described in documents. Alternatively, a commercially available vector system, such as piGENE™ U6 vector and piGENE™ H1 vector (TAKARA BIO INC., Kyoto, Japan) can also be used (T. R. Brummelkamp et al., Science (2002), 296: 550-553; N. S. Lee et al., Nature Biotech. (2002), 20: 500-505; M. Miyagishi et al., Nat. Biotechnol. (2002), 20: 497-500; P. J. Paddison et al., Genes & Dev. (2002), 16: 948-958; T. Tusch, Nature Biotech (2002), 20: 446-448; C. P. Paul et al., Nature Biotech. (2002), 20: 505-508; Edited by Kazumasa Tahira et al., RNAi Experimental Protocols, YODOSHA (Tokyo, Japan), 2003).

Another nucleic acid that is an active ingredient of the composition of the present invention is ribozyme. Ribozyme is RNA having catalytic activity and has activity of cleaving mRNA that corresponds to a target IRBIT gene of the present invention. The expression of the gene is inhibited or suppressed by this cleavage.

It is known that a cleavable target sequence of ribozyme is generally NUX (N=A, G, C, U; X=A, C, U), such as a sequence containing GUC triplet. Such ribozyme contains hammerhead-type ribozyme. The hammerhead-type ribozyme can contain a nucleotide sequence that composes a sensor site, a nucleotide sequence that contains a region capable of forming cavities that stably capture $Mg^{2+}$ ion only when RNA binds to the sensor site, and a nucleotide sequence containing a region complementary to a sequence in the vicinity of the cleavage site of the target RNA.

For delivery of the ribozyme of the present invention into cells or into a patient's living body, ribozyme is enclosed within liposome (preferably, positively charged liposome) (JP Patent Publication (Kokai) No. 9-216825 A (1997)) and then the liposome is incorporated into a viral vector such as an Adeno-associated virus (JP Patent Publication (Kohyo) No. 2002-542805 A). With the use of these methods, a drug delivery system can be constructed.

Ribozyme can be incorporated into a vector so that it can be expressed. Examples of a promoter for expression of ribozyme include pol II and pol III promoters. A promoter is preferably a pol III promoter such as a mammal-derived tRNA promoter and is more preferably a tRNA$^{Val}$ promoter (S. Koseki et al., J. Virol., 73: 1868-1877, 1999).

Antibody

An antibody against IRBIT or a fragment thereof can also be used for controlling the above biological functions.

Examples of such antibody include polyclonal antibodies, monoclonal antibodies, recombinant antibodies, human antibodies, humanized antibodies, chimeric antibodies, single-chain antibodies, Fab fragments, F (ab')$_2$ fragments, Fv, scFv, bispecific antibodies, and synthetic antibodies.

The class or subclass of an antibody may be any type. Examples of such class or subclass include IgG IgM, IgE, IgD, IgA, IgG$_1$, IgG$_2$, IgG$_3$, IgG$_4$, IgA$_1$, and IgA$_2$.

An antibody to be used herein may also be derivatized via pegylation, acetylation, glycosylation, amidation, or the like.

For preparation of a polyclonal antibody, a water-in-oil emulsion containing IRBIT as an immunogen (approximately 1 μg to 100 μg) and if necessary an adjuvant such as Freund's complete or incomplete adjuvant, aluminium hydroxide (alum), muramyldipeptide, or lipid A is injected intradermally or intravenously for immunization into non-human animals such as rabbits, guinea pigs, mice, rats, sheep, or goats. Approximately 2 to 4 weeks later, boost was performed via injection once or twice with adjuvant-free IRBIT. Blood was collected on a trial basis, so as to confirm that the antibody titer has increased sufficiently. Subsequently, blood was collected from the animals and then antiserum was collected by centrifugation. If necessary, purification is performed by ammonium sulfate fractionation, DEAF ion exchange chromatography, or the like, so that IgG can be obtained.

A hybridoma that secretes a monoclonal antibody can be prepared according to Kohler and Milstein's technique (Nature 1975, 256: 495-497). Specifically, a hybridoma can be obtained by extracting the spleen or the lymph node from an immunized animal, fusing antibody-producing cells contained therein to myeloma cells derived from a mammal such as a mouse, a rat, or a guinea pig, and then performing HAT selection. Cell fusion can be performed using polyethylene glycol (e.g., molecular weight ranging from 1500 to 6000), for example. For production of a target antibody, the reactivity of the hybridoma to the immunizing antigen in a culture supernatant can be measured using a conventional method such as enzyme immunoassay, radioimmunoassay, or a fluorescent antibody technique.

Furthermore, for preparation of a monoclonal antibody from a hybridoma, a hybridoma is cultured in vitro and then the monoclonal antibody may be isolated from the culture supernatant. Alternatively, a hybridoma is cultured in vivo in the ascite or the like of a mouse, a rat, a guinea pig, or the like and then the monoclonal antibody may be isolated from the ascites.

Alternatively, a gene that encodes a monoclonal antibody is cloned from antibody-producing cells such as hybridomas, and then the resultant is incorporated into a vector, and then the vector is introduced into mammalian cells (e.g., CHO), so that a recombinant antibody can also be prepared (P. J. Delves et al., ANTIBODY PRODUCTION ESSENTIAL TECHNIQUES., 1997, John Wiley & Sons).

A human antibody can be produced by a pharge display library method (T. C. Thomas et al., Mol. Immunol. 33: 1389-1401, 1996) or a method using a human antibody-producing animal (e.g., a mouse or cattle) (I. Ishida et al., Cloning Stem Cell 4: 91-102, 2002), for example.

For example, a human antibody-producing mouse can be produced by a method that involves introducing a human chromosome fragment containing a human-antibody-producing gene into a human artificial chromosome, incorporating the artificial chromosome into a mouse embryonic stem cell or the like with the use of a microcell method, injecting the recombinant embryonic stem cell into a blastcyst, implanting the blastcyst in the uterus of a foster mother mouse, causing the mouse to deliver chimeric mice, and thus producing homozygous progeny mice that contains the human antibody gene and is capable of producing human antibodies through mating of male and female chimeric mice or mating of chimeric mice with wild-type mice (e.g., Japanese Republication (Saikohyo) No. 02/092812 A (1990), International Publication WO 98/24893, and WO 96/34096). The human-antibody-producing transgenic mouse is immunized with the IRBIT protein of the present invention as an antigen, the spleen is excised, and then a hybridoma is formed by fusing the spleen cells with mouse myeloma cells, so that a target monoclonal antibody can be selected.

The pharge display library method involves screening for DNA that encodes a target antibody from the immunoglobulin gene library directly obtained from untreated human lymphocytes and then establishing physical association between the DNA and the antibody chain with the use of phage particles, thereby enriching the phages presenting the antibody having affinity for the target via affinity screening. With the use of this method, an antibody having binding affinity for a target can be synthesized in a large amount by general techniques (e.g., JP2003-527832 A).

The composition of the present invention can be used for treatment of diseases or disorders.

Therapeutic Composition

The present invention is associated with such diseases or disorders caused by abnormalities in protein synthesis, phosphatidylinositol metabolism, and intracellular pH.

In the case of protein synthesis, the protein synthesis associated with the binding of IRBIT to CPSF is controlled. In this case, IRBIT suppresses protein synthesis and a substance that suppresses the functions of IRBIT (the above nucleic acid or antibody) can enhance protein synthesis. An example of an abnormality in protein synthesis, in which CPSF is involved, is tumor.

In the case of phosphatidylinositol metabolism, one example of diseases associated with abnormal activation of PIPKII is type 2 diabetes. IRBIT has an effect of suppressing PIPKII activity, so that IRBIT can be used for treatment of type 2 diabetes.

In the case of intracellular pH, pNBC1 plays an important role in maintenance of intracellular pH. In particular, examples of diseases caused by such pH approaching or changing to acidic levels include eye diseases such as glaucoma and cataract and diseases such as dwarfism, mental retardation, and pancreatitis. IRBIT binds to pNBC1, so as to make it possible to maintain intracellular pH at a normal level.

The content of an active ingredient of the composition of the present invention ranges from, but is not limited to, approximately 1 μg to 100 mg. The content can be varied depending on the types of active ingredient.

The dose of IRBIT in the composition of the present invention ranges from approximately 1 μg to 1 mg and preferably approximately ranges from 50 μg to 500 μg per dosage unit, but is not limited to such ranges.

The dose of nucleic acid in the composition of the present invention ranges from, in terms of siRNA, antisense nucleic acid, or ribozyme, approximately 1 nM to 100 μM and preferably approximately ranges from 10 nM to 50 μM per dosage unit, but is not limited thereto.

The dose of an antibody or a fragment thereof in the composition of the present invention ranges from, but is not limited to, approximately 1 to 100 mg/ml and preferably approximately 5 to 70 mg/ml per dosage unit.

However, the above dose or dosage can be varied depending on conditions, age, sex, severity, or the like of a patient and should be determined based on the judgment made by a medical specialist.

The composition of the present invention can generally contain a pharmaceutically acceptable carrier (specifically, an excipient or a diluent), such as sterilized water, physiological saline, buffer, or nonaqueous liquid (e.g., oil of almonds, plant oil, or ethanol). The composition can further contain a pharmaceutically acceptable stabilizer (e.g., an amino acid such as methionine), a preservative (methyl p-hydroxybenzoate or sorbic acid), an isotonic agent (e.g., sodium chloride), an emulsifying agent (e.g., lecithin or gum arabic), a suspending agent (e.g., a cellulose derivative), or the like.

Examples of preferable pharmaceutical preparations include solutions, suspending agents, and emulsifying agents.

Examples of the route of administration of the composition of the present invention include oral administration and parenteral administration (e.g., intravenous administration and local administration). Examples of local administration include surgical operation or a method that involves direct endoscopic injection into an affected part. Furthermore, the composition of the present invention can be administered in a single or in divided doses to a patient based on the treatment plan determined by a medical specialist at constant time intervals of 1 week, 2 weeks, 3 weeks, 1 month, 2 months, 6 months, 1 year, or the like.

Furthermore, an antibody or a fragment thereof can be delivered to a patient as described below. Such an antibody or a fragment thereof alone or the same encapsulated within a liposome (preferably, positively charged liposome), a microcapsule, nanoparticle, or the like is delivered in combination with generally an appropriate carrier (an excipient or a diluent) via oral or parenteral route (e.g., intravenous administration or local administration).

The composition of the present invention can be used in vitro, in vivo, or ex vivo.

In vitro, the composition of the present invention can be used for screening for substances for treatment (see below).

Ex vovo, cells or tissues that have been once removed from the patient's body can be returned to the body after treatment with the active ingredients of the present invention. Accordingly, cells or tissues in which abnormalities occur in protein synthesis, phosphatidylinositol metabolism, or intracellular pH can be caused to return to a normal state.

2. Use Examples of IRBIT

The present invention further provides the following uses of IRBIT in vitro or ex vivo.

First, the present invention provides a use of IRBIT in control of intracellular protein synthesis in vitro or ex vivo.

This method is based on the fact that IRBIT has an effect of binding to CPSF, thereby controlling CPSF functions.

Second, the present invention provides a use of IRBIT in control of intracellular phosphatidylinositol metabolism in vitro or ex vivo.

This method is based on the fact that IRBIT has an effect of suppressing PIPKII activity.

Third, the present invention provides a use of IRBIT in control of intracellular pH in vitro or ex vivo.

This method is based on the fact that IRBIT has an effect of activating pNBC1. Moreover, the activation of pNBC1 requires phosphorylation of IRBIT.

As described above, IRBIT can be used in vitro for screening for a substance that makes it possible to control intracellular protein synthesis, phosphatidylinositol metabolism, or intracellular pH. Furthermore, IRBIT can be used ex vivo for causing abnormal conditions of cells or tissues (including abnormal protein synthesis, abnormal phosphatidylinositol metabolism, or abnormal intracellular pH) to return to normal conditions.

3. Screening

The present invention further provides a method for screening for a substance, comprising measuring the binding of IRBIT to CPSF, PIPKII, or pNBC1 in the presence of candidate substances and then identifying a substance that suppresses or enhances the binding.

Regarding the above binding, the binding of IRBIT to CPSF, PIPKII, or pNBC1 can be measured in vitro or within cells (in particular, mammalian cells) in the presence of candidate substances. Examples of mammalian cells include CHO, COS, HEK293, HeLa, and NIH3T3.

The thus identified substance can be used for treatment or diagnosis, for example. In particular, such substance controls at least one intracellular biological function selected from the group consisting of intracellular protein synthesis, phosphatidylinositol metabolism, and intracellular pH.

When the above binding is performed in vitro, for example, IRBIT and CPSF, PIPKII, or pNBC1 are caused to present in an appropriate buffer, a candidate substance is added to the buffer, and then the level of binding of IRBIT to CPSF, PIPKII, or pNBC1 can be detected by SDS-PAGE and the immunoblot method. This system is effective for detection of a substance that suppresses or inhibits the above binding. The recombinant protein of IRBIT, CPSF, PIPKII, or pNBC1 can be prepared by techniques similar to those described in the section of the above IRBIT.

When the binding is performed within cells, DNAs encoding the following proteins are incorporated into the same vector or different vectors so that IRBIT and CPSF, PIPKII, or pNBC1 can be expressed simultaneously or separately and then mammalian cells are transformed or transfected with the vectors. The translated proteins are caused to present within cells and particularly in the cytoplasms. Preferably, vector DNA contains no secretion signal sequence.

The amino acid and nucleotide sequences of CPSF, PIPKII, or pNBC1 are available from the GenBank, from documents, or the like. The amino acid and nucleotide sequences are deposited under accession Nos: AB092504; AF030558 and AF033355; or NM 003759 and NM 018760; respectively. The amino acid and nucleotide sequences of IRBIT are as described above.

Expression vectors are any vectors that can be used in preferably mammalian cells. A vector can contain regulatory sequences such as a promoter, an enhancer, a replication origin, a ribosome-binding site, a multicloning site, a terminator, and poly A signal. As an expression vector, a commercially available vector such as pSG5, pXT1 (Stratagene), pSVK3, pBPV, pMSG and pSVL SV40 (Pharmacia), pHM6, pVM6, and pXM (Roche Diagnostics) can be adequately selected and used.

Examples of a promoter include a CMV promoter, an SV40 promoter, and an EF promoter.

Examples of a method for introducing DNA encoding IRBIT, CPSF, PIPKII, or pNBC1 into host cells include a calcium phosphate method, a lipofection method, an electroporation method, and methods using viral infection with adenovirus, retrovirus, or the like (Experimental Medicine, Separate Volume, 4$^{th}$ edition, edited by Masami Matsumura et al., "New genetic engineering handbook" (2003) YODOSHA, Tokyo, Japan).

Alternatively, non-human transgenic animals (e.g., mice) are produced by incorporating an IRBIT gene exogeneously into the genome by a known technique using oocytes or embryonic stem cells of a non-human animal so that the gene can be forcedly expressed. Furthermore, non-human transgenic animals (e.g., mice) are produced by incorporating a CPSF, PIPKII, or pNBC1 gene exogeneously into the genome, so that the gene can be forcedly expressed. Non-human chimeric animals and their progenies can thus be produced by mating both transgenic animals and then producing non-human chimeric animals and their progenies capable of expressing the IRBIT gene and the CPSF, PIPKII, or pNBC1 gene.

The ways in which the binding of IRBIT (forcedly expressed within cells or within a non-human transgenic animal) to CPSF, PIPKII, or pNBC1 is affected in the presence of candidate substances incorporated within cells or animals are examined by measuring the binding according to a pull down method, an immunoprecipitation method, or the like. At the same time, the effects on intracellular synthesis of a specific protein, the effects of the aforementioned binding on phosphatidylinositol metabolism, and the effects on intracellular pH are examined.

The effects on intracellular protein synthesis can be measured by the Western blot method or the like using an antibody against a specific protein, for example.

The effects on phosphatidylinositol metabolism can be measured via quantification of PIP2 level using a [$^3$H] label or a PIP2-binding protein, for example.

The effects on intracellular pH can be measured by intracellular pH measurement or the like using a fluorescent pH indicator or the like.

Examples of candidate substances include, but are not limited to, organic small molecules, peptides, polypeptides, proteins, nucleosides, oligonucleotides, polynucleotides, and nucleic acids (DNA or RNA).

As described above, IRBIT has extremely important significance for all cells in regulation of intracellular metabolism, pH change, ion balance, and phospholipid metabolism, control of protein synthesis, control of $Ca^{2+}$ release, and the like. It has been revealed herein that through control of IRBIT concentration or expression pattern, various biological functions described above can be controlled. Substances that are identified by the screening method of the present invention are useful for such control.

EXAMPLES

Hereinafter, the present invention will be described in detail by examples as follows, but the scope of the present invention is not limited by these examples.

Example 1

Involvement of IRBIT in Cytoplasmic Poly (A) Addition Reaction

CPSF is a group of conjugated proteins consisting of 4 subunits: CPSF160, CPSF100, CPSF73, and CPSF30. First, to reveal to which one of the 4 subunits IRBIT binds, myc-tagged cDNAs prepared by tagging each subunit with myc were expressed together with IRBIT in various combinations by COS cells or the like and then the way in which coprecipitation occurs upon immunoprecipitation of IRBIT or CPSF was examined.

Mouse-derived CPSF was used herein. CPSF was cloned by RT-PCR based on the full-length sequence under GenBank accession No. AB092504 and the nucleotide sequence of each of four subunits (H. Ando et al., 2003, ibid). Mouse-derived IRBIT was used herein. IRBIT was cloned by RT-PCR based on the nucleotide sequence under GenBank accession No. NM_145542 (H. Ando et al., 2003, ibid).

DNA was prepared by fusing DNA encoding an myc tag to cDNA encoding the full-length of or each subunit of CPSF. The thus prepared DNA was inserted into a vector for mammals. Meanwhile, cDNA encoding IRBIT was also inserted into the same vector. COS cells were transformed with the thus prepared vector and then the above DNA was co-expressed.

Cells were separated by centrifugation and then lysed. Cytoplasmic fractions were collected and then the binding of IRBIT to CPSF was detected using an anti-IRBIT antibody (JP2004-129612 A) and an anti-myc antibody.

As a result, IRBIT was revealed to bind to CPSF via the CPSF160 subunit (FIG. 1).

Furthermore, a similar experiment conducted using CPSF160 deletion mutants revealed that IRBIT binds to the mRNA binding site of CPSF160 (FIG. 2).

The mRNA binding site of CPSF160 is a region essential for CPSF to recognize mRNA to which poly (A) is added. Hence, the fact that IRBIT binds to this region suggests that IRBIT may inhibit CPSF functions. To confirm this, the binding of IRBIT with CPSF and the effects of the binding on polyadenylation reaction were examined with the use of an in vitro rearrangement system using purified proteins.

CPSF is a molecule essential for mRNA polyadenylation reaction, but the location at which CPSF functions is mainly within the nucleus. CPSF functions for RNA just after its transcription from DNA; that is, CPSF functions as a member involved in the process of the maturation reaction of such RNA until the RNA is released from the nucleus in the form of mRNA. However, exceptionally, in other situations such as in the process of oocyte maturation or local synthesis of new proteins in neurons, CPSF is involved in cytoplasmic mRNA polyadenylation and regulates the length of poly (A), so as to regulate the protein synthesis of a target molecule (Daron C. Barnard et al., Cell 2004, 119: 641-651). This cytoplasmic polyadenylation reaction is an exceptional phenomenon, but is an essential phenomenon for oocyte maturation and the establishment of neuroplasticity. When the intracellular distribution of IRBIT is examined, almost no IRBIT is present within the nucleus. Accordingly, the present inventors conducted examinations with a focus on the involvement of IRBIT in cytoplasmic polyadenylation reaction.

A *Xenopus* oocyte system is better for examination of cytoplasmic polyadenylation reaction. Hence, the present inventors first performed cloning and isolation of IRBIT cDNA from *Xenopus* oocytes according to a standard method. Unlike mammalian cells, 3 types of IRBIT mRNAs were expressed in *Xenopus* oocytes, and the 3 types of IRBIT mRNAs were revealed to bind to CPSF160.

The 3' terminus of $IP_3$ receptor mRNA has a sequence that may be subjected to a cytoplasmic polyadenylation reaction. Actually, in cerebellum Purkinje cells, the mRNA is present within dendrites. This suggests the possibility that IRBIT released from the $IP_3$ receptor controls $IP_3$ receptor protein synthesis via binding with CPSF.

Moreover, the present inventors discovered that IRBIT has an effect of further suppressing polyadenylation activity in the presence of PAP and Fip1 (CPSF subunits) (I. Kaufmann et al., EMBO J. (2004) 23: 616-626).

It was demonstrated based on the above results that IRBIT controls protein synthesis via the binding to CPSF within cells.

Example 2

Interaction Between IRBIT and PIP Kinase Type II (PIPKII)

The present inventors further searched for molecules that interact with IRBIT. With procedures similar to those used in Example 1, FLAG-IRBIT was overexpressed in HEK293 cells, immunoprecipitation was performed using an anti-FLAG antibody, and then proteins that had been coprecipitated with IRBIT were analyzed using a mass spectroscopic analyzer. As a result, phosphatidylinositol-5-phosphate 4-kinase$\gamma$ (PIPKII$\gamma$), which is an enzyme for phosphorylating phospholipids, was identified. The PIPKII family (PIPKII$\alpha$, PIPKII$\beta$, and PIPKII$\gamma$) is the family of enzymes involved in the synthesis of $PIP_2$. In view of the fact that $IP_3$ is produced by hydrolysis of $PIP_2$, a signaling mechanism in which the $IP_3$ receptor, IRBIT, and PIPKII$\gamma$ are involved may be present (FIG. 3).

Furthermore, the following experiment was conducted and the results are as described below.

(1) Mouse IRBIT and Myc-PIPKII$\alpha$, $\beta$, or $\gamma$ were over-expressed in COS-7, followed by immunoprecipitation. Specifically, cells were solubilized with a lysis buffer (10 mM Hepes, 100 mM NaCl, 2 mM EDTA, 1% P-40, pH 7.4) and then centrifuged (20000×g, 30 minutes) to collect supernatants. Subsequently, an anti-Myc antibody or an anti-IRBIT antibody was added and then reaction was performed for 1 hour. Furthermore, protein G Sepharose® was added before one hour reaction, and the immune complex was washed with a lysis buffer and then eluted with a SDS-PAGE sample buffer. Subsequently, Western blotting was performed using an anti-Myc antibody or an anti-IRBIT antibody. As a result, IRBIT was coprecipitated with Myc-PIPKII$\alpha$, $\beta$, and $\gamma$ (FIG. 4).

Figure 5:
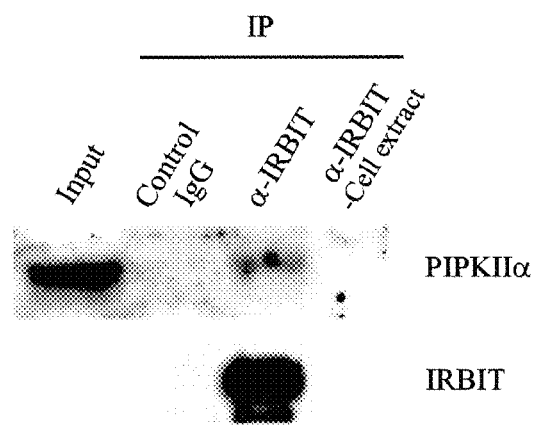
FIG. 5 shows coprecipitation of mouse cerebellum PIPKIIα with an anti-mouse IRBIT antibody by immunoprecipitation. "Input" is as described in FIG. 4.

(2) Immunoprecipitation was performed using an anti-IRBIT antibody and the mouse cerebellum, so that PIPKII$\alpha$ was coprecipitated (FIG. 5). The in vivo binding of IRBIT with PIPKII was confirmed based on the results.

Figure 6:
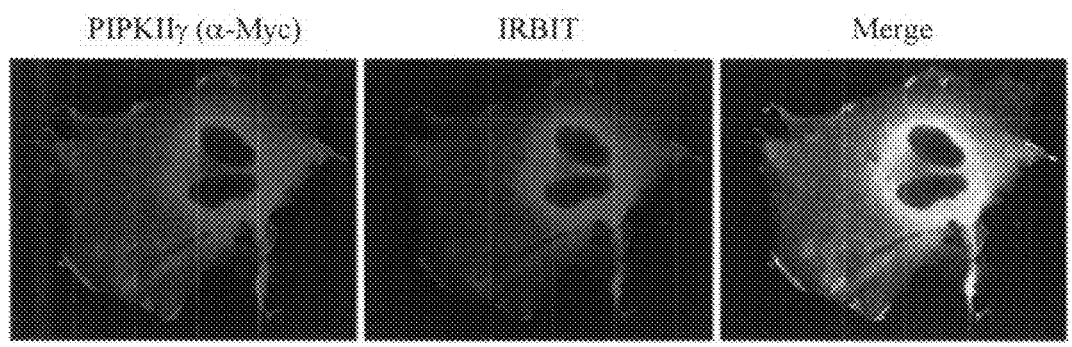
FIG. 6 shows that both IRBIT and Myc-PIPKIIγ are localized in the cytoplasm. "Merge" denotes merged images of a stained PIPKII image and a stained IRBIT image. Merged portions are observed yellow.

(3) Mouse IRBIT and Myc-PIPKII$\gamma$ were overexpressed in COS-7 and then immunostaining was performed. Specifically, after fixation with 4% paraformaldehyde, transmembrane treatment with 0.1% Triton X-100 and blocking treatment with 2% goat serum were performed, a mouse anti-Myc antibody and a rabbit anti-IRBIT antibody were added, and then reaction was performed at room temperature for 1 hour. Alexa488-conjugated anti-mouse IgG antibody and Alexa594-conjugated anti-rabbit IgG antibody were added as secondary antibodies, followed by 45 minutes of reaction at 37° C. As a result, both IRBIT and Myc-PIPKIIγ were revealed to be localized within the cytoplasms (FIG. 6).

Figure 7:
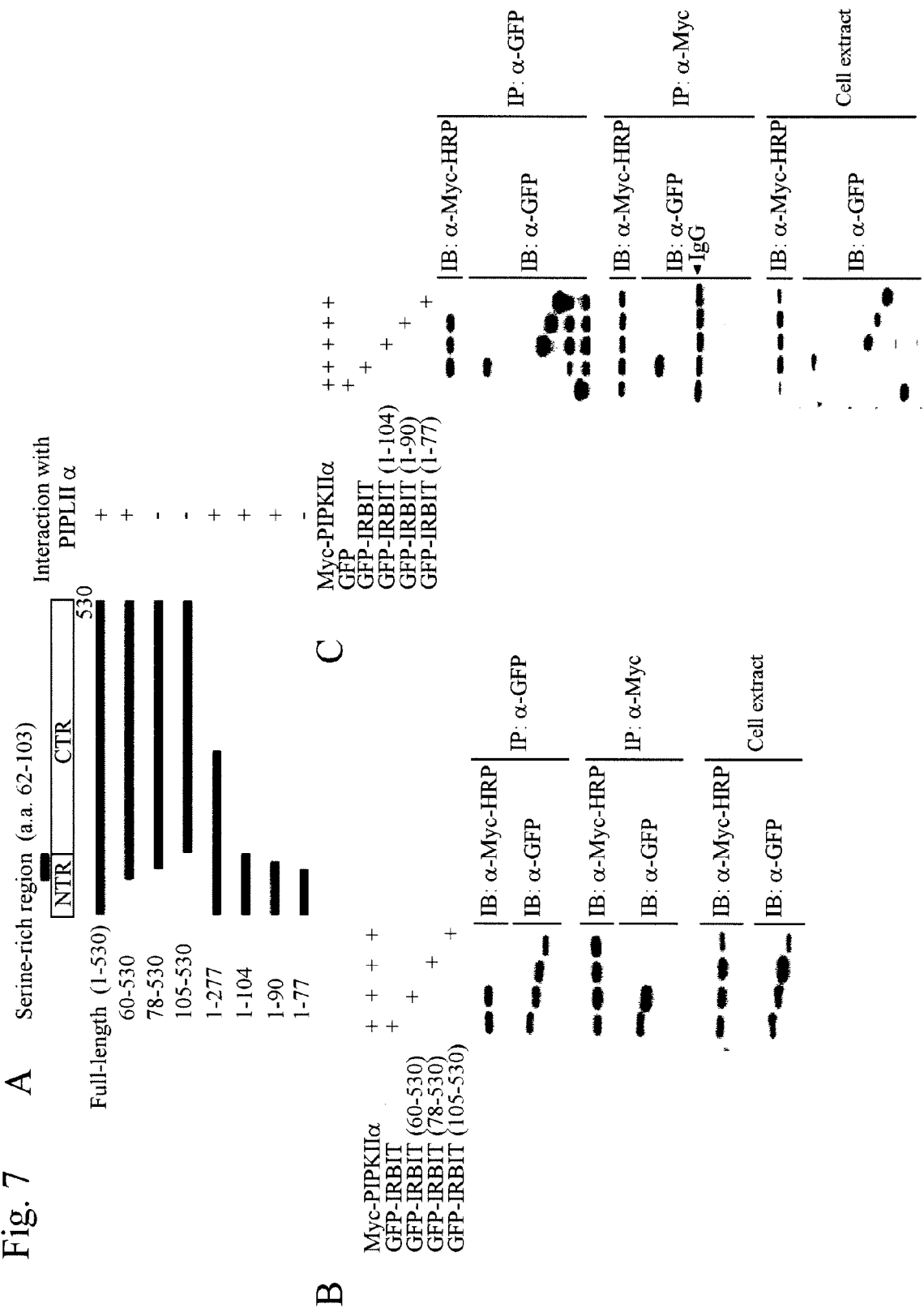
FIG. 7 shows identification of the binding site of IRBIT and PIPKII using IRBIT deletion mutants.

(4) Mouse IRBIT deletion mutants (60-530, 78-530, 105-530, 1-277, 1-104, 1-90, and 1-77 in the amino acid sequence of SEQ ID NO: 3) were prepared by amplifying the corresponding sequences by PCR and then cloning them into GFP fusion protein expression vectors pEGFP-C1 (Clontech). The binding of each of these mutants with PIPKIIα was examined, revealing that a serine-rich region existing in the N-terminal region of IRBIT is important for the above binding (FIG. 7).

Figure 8:
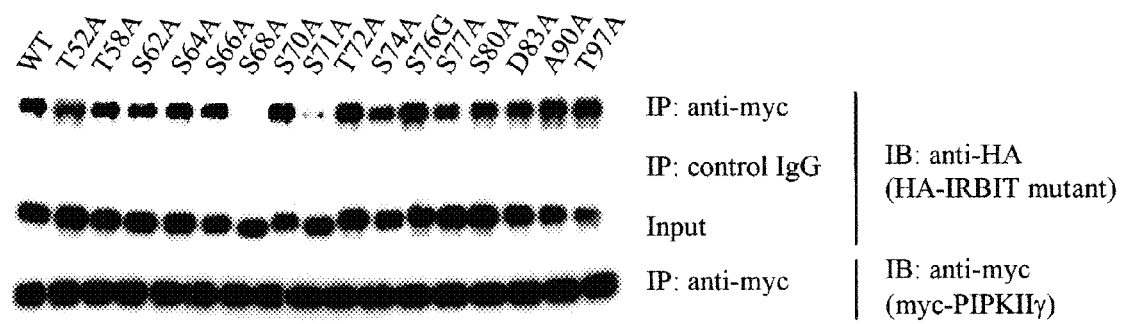
FIG. 8 shows that Ser68 and Ser71 of IRBIT bind to PIPKII.

(5) Point mutants (T52A, T58A, S62A, S64A, S66A, S68A, S70A, S71A, T72A, S74A, S76G, S77A, S80A, D83A, S90A, and T97A in the amino acid sequence of SEQ ID NO: 3) of the mouse IRBIT serine-rich region were prepared using a site-directed mutagenesis kit (Stratagene). The binding of each of these mutants with PIPKIIα was examined. As a result, IRBIT Ser68 and Ser71 were found to be important for the above binding (FIG. 8).

It was confirmed based on the above results that IRBIT binds to the PIPKII family. Furthermore, IRBIT suppresses PIPKII activity, as revealed from preliminary data. Thus, it was concluded that IRBIT controls the activity of phosphatidylinositol metabolism.

Example 3

Activation of NBC1 (Na/HCO$_3$ Cotransporter 1) by IRBIT

The present inventors further identified an NBC1 (sodium bicarbonate co-transporter 1) protein as a protein that binds to IRBIT, which transports sodium ions and bicarbonate on the cell membrane.

It is known that NBC1 includes two splicing mutants, p type and k type (Seth L. Alper, Annu. Rev. Physiol. 2002, 64: 899-923). It was revealed that IRBIT binds to p-type NBC1 (referred to as pNBC1) of these mutants and that the binding of IRBIT to pNBC1 requires phosphorylation of some serine residues in IRBIT. Experiments and results conducted are as specifically described below.

(1) Identification of IRBIT-Binding Region of pNBC1

The p-type-specific N-terminal sequence (amino acids 1-85) of pNBC1 was revealed to be essential for binding with IRBIT. Other deletion mutants were prepared within the 85 amino acids, and then the binding of these mutants with IRBIT was studied using pull down assay. Specifically, the following experiment was conducted.

HA-IRBIT was overexpressed in COS-7 cells and then cell extracts were prepared. A recombinant protein of a MBP-pNBC1 deletion mutant was added. After reaction, the bound proteins were pulled down with an amylose resin. HA-IRBIT was detected by Western blotting using an anti-HA antibody.

As a result, it was demonstrated that binding with IRBIT is possible if the 62 N-terminal amino acids of the p-type-specific sequence are present (FIG. 9 and FIG. 10). However, if an N-terminal portion or a C-terminal portion was deleted from the 62 amino acids, the binding with IRBIT became impossible to observe. Thus, it was concluded that an IRBIT-binding region with a length shorter than the 62 amino acids makes it difficult for the binding to take place. It was suggested based on the results that a sequence with a length of several specific amino acids of pNBC1 is not involved in the binding with IRBIT, but rather that a three-dimensional structure comprising dozens of amino acids may be required for binding with IRBIT.

(2) Identification of pNBC1-Binding Region of IRBIT

Next, various mouse IRBIT (full-length 530 amino acids; SEQ ID NO: 3) deletion mutants were expressed in COST cells and then the ability of each mutant to bind to pNBC1 was examined by pull down assay. Specifically, the following experiment was conducted.

GFP-IRBIT deletion mutants were overexpressed in COS-7 cells and then cell extracts were prepared. A MBP-pNBC1 (1-85) recombinant protein was added. After reaction, the bound proteins were pulled down with an amylose resin. GFP-IRBIT deletion mutants were detected by Western blotting using an anti-GFP antibody.

The results are shown in FIG. 11. As shown in FIG. 11, it was demonstrated that even deletion mutants (1-104 and 1-277) expressing the IRBIT N-terminal portions (confirmed to bind to the IP$_3$ receptor) were unable to bind to pNBC1. Moreover, the deletion mutant (105-530) expressing an IRBIT C-terminal portion (previously confirmed to be unable to bind to the IP$_3$ receptor) was also unable to bind to pNBC1. A serine phosphorylation site demonstrated to be necessary for binding with pNBC1 is completely contained within 1-104. Thus, it was considered that although a short pNBC1-binding sequence is present in 1-104, the binding with pNBC1 may be inhibited by some kind of three-dimensional structure. Hence, deletion mutants were prepared via further fine deletion of 1-104, and then the binding of each of these mutants with pNBC1 was analyzed. However, none of these mutants were observed to bind to pNBC1.

Based on the above results, it was revealed that the entire structure, including the IRBIT N-terminus and the C-terminus, is required for binding with pNBC1. It was also revealed that the binding manner of IRBIT with pNBC1 is different from that of IRBIT with IP$_3$ receptor, and such binding can be achieved only in the presence of the IRBIT N-terminus.

(3) Binding of Endogenous IRBIT with NBC1

Next, an experiment was conducted to confirm the binding of endogenous IRBIT to NBC1 using immunoprecipitation.

NBC1 had been previously identified as an IRBIT-binding protein in a cerebellum membrane fraction. First, immunoprecipitation was performed using a cerebellum membrane fraction extract. Furthermore, since IRBIT is known to also bind to an IP$_3$ receptor in a cerebellum membrane fraction, whether or not a triple complex of NBC1, IRBIT, and an IP$_3$ receptor could be formed was examined. Specifically, the following experiment was conducted.

After solubilization of the cerebellum membrane fraction with a surfactant, an anti-IRBIT antibody, an anti-NBC antibody, or a control antibody was added to perform a reaction. Moreover, protein G Sepharose® was added to extract immune complexes. Subsequently, Western blotting was performed using the anti-IRBIT antibody, the anti-NBC antibody, or the anti-IP$_3$R antibody.

Figure 12:
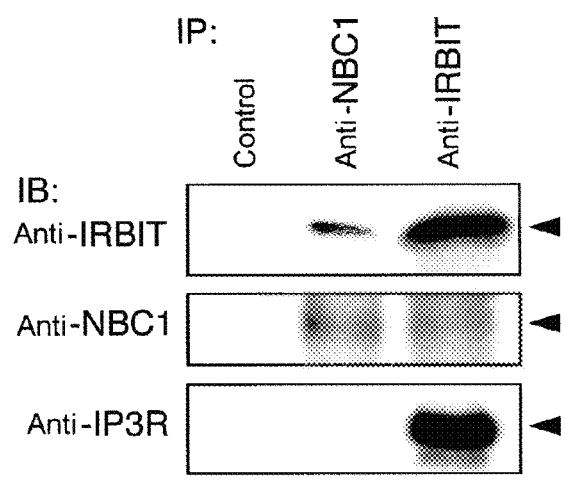
FIG. 12 shows the binding of endogenous IRBIT and NBC1 in cerebellum membrane fractions. A cerebellum membrane fraction extract was subjected to immunoprecipitation (IP) using a preimmunization antibody as a control and an anti-NBC1 antibody, or an anti-IRBIT antibody. Precipitates were subjected to SDS-PAGE and then Western blotting (IB) using an anti-IRBIT antibody, an anti-NBC1 antibody, or an anti-$IP_3$ receptor antibody was performed. Black triangle (◄) indicates an electrophoretic movility of each protein.

As a result, it was revealed that the anti-NBC1 antibody immunoprecipitate contained endogenous IRBIT and the anti-IRBIT antibody immunoprecipitate contained endogenous NBC1. Thus it was confirmed that endogenous IRBIT and NBC1 form a complex in a cerebellum membrane fraction (FIG. 12). Meanwhile, as already reported by Ando et al., (2003, ibid), the IP$_3$ receptor was detected in the anti-IRBIT immunoprecipitate, but no IP$_3$ receptor could be detected in the anti-NBC1 precipitate. These results demonstrate that most of the endogenous NBC1 does not form any triple complex containing IRBIT and the IP$_3$ receptor.

Furthermore, to confirm that the binding of IRBIT to NBC1 is universal, the binding of endogenous IRBIT to NBC1 was examined by the immunoprecipitation similar to the above method using COST cell extracts. Specifically, the following experiment was conducted.

An anti-IRBIT antibody, an anti-NBC antibody, or a control antibody was added to the COS-7 cell extract to perform a reaction. Moreover, protein G Sepharose® was added to extract immune complexes. Subsequently, Western blotting was performed using an anti-IRBIT antibody or an anti-NBC antibody.

Figure 13:
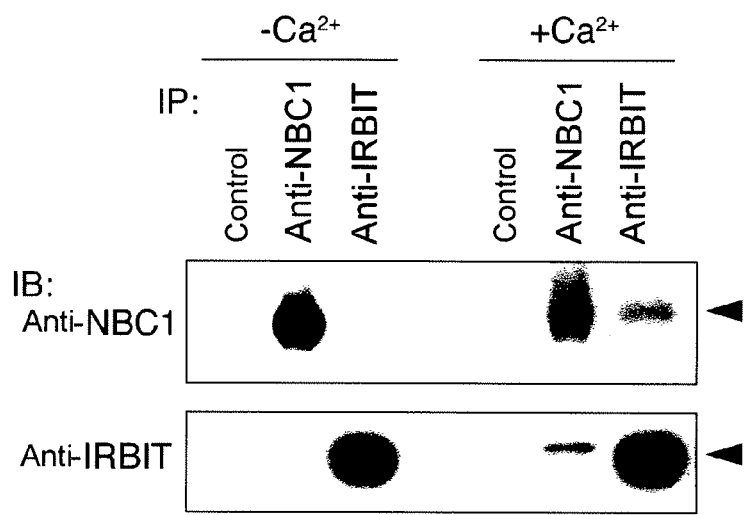
FIG. 13 shows the binding of endogenous IRBIT and NBC1 in COS7 cell extracts. The COS7 cell extract was subjected to immunoprecipitation (IP) using a preimmunization antibody (control), an anti-IRBIT antibody, or an anti-NBC1 antibody. Precipitates were subjected to SDS-PAGE and then Western blotting (IB) using an anti-NBC1 antibody or an anti-IRBIT antibody was performed. Black triangle (◄) indicates an electrophoretic movility of each protein. Three rows on the left show the results obtained using precipitates from immunoprecipitation in the absence of $CaCl_2$, and three rows on the right show the results obtained using precipitates from immunoprecipitation in the presence of $CaCl_2$.

FIG. 13 shows the results. As shown in FIG. 13, when COS7 cells were extracted with the same buffer as that used for preparation of a cerebellum membrane fraction extract, no binding of endogenous IRBIT to NBC1 was detected. However, when a similar experiment was conducted with addition of 2 mM $CaCl_2$ to the buffer, the binding of endogenous IRBIT to NBC1 was detected. This buffer had contained 2 mM EDTA in advance, so it was considered that the calcium ion concentration was several μM when 2 mM $CaCl_2$ was added. These results suggest that the binding of endogenous NBC1 to IRBIT might be controlled differently (i.e., in different manners) in a cerebellum membrane fraction and COS7 cells.

(4) Activation of NBC1 by IRBIT

Mouse IRBIT cRNA and the cRNA of human pNBC1 or kNBC1 were simultaneously injected into cultured cells of *Xenopus* oocytes. The membrane potential was set at −25 mV, and then current changes were measured when an ND96 solution (96 mM NaCl, 2 mM KCl, 1 mM $MgCl_2$, 5 mM HEPES, and pH 7.4) was replaced by an ND96+$HCO_3^-$ solution. As controls, IRBIT, pNBC1, and kNBC1 were used.

As a result, only the pNBC1 activity was enhanced approximately 6 to 7 times by simultaneous injection of IRBIT (FIG. 14A). Similarly, when the membrane potential was varied within a range from −160 mV to +60 mV in the ND96+ $HCO_3^-$ solution, only the pNBC1 activity was significantly enhanced by simultaneous injection of IRBIT (FIG. 14B).

Furthermore, an IRBIT mutant (S68A, S71A, S74A, or S77A) was prepared in which an IRBIT phosphorylation site had been substituted with alanine (A). The cRNA of the IRBIT mutant and the cRNA of human pNBC1 were simultaneously injected into *Xenopus* oocytes in a manner similar to the above. The membrane potential was set at −25 mV, and then current changes were measured when the ND96 solution was replaced by the ND96+$HCO_3^-$ solution.

Figure 15:
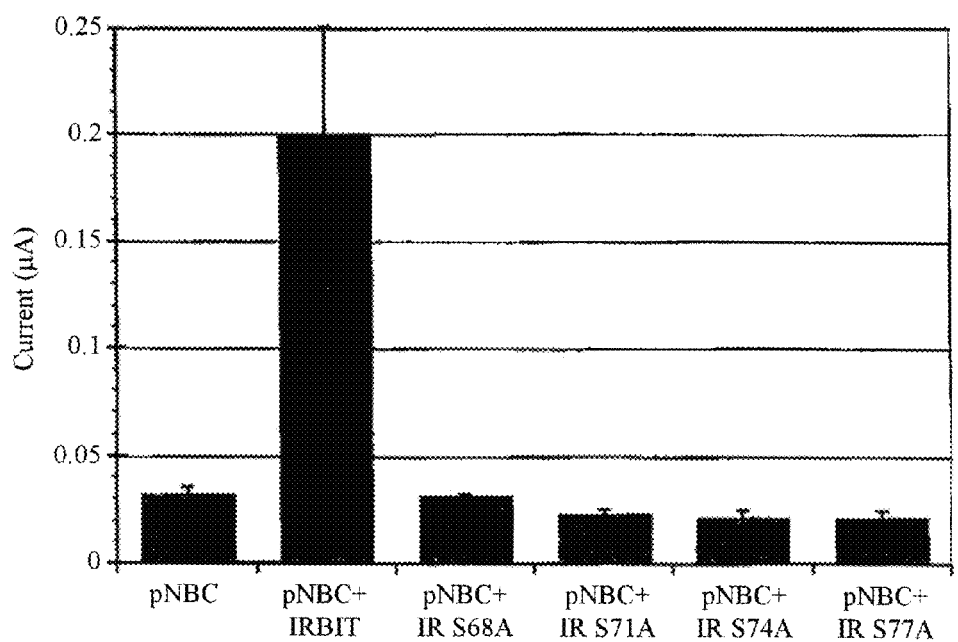
FIG. 15 shows that phosphorylation of IRBIT is required for activation of pNBC1.

As a result, the effects of IRBIT to enhance the pNBC1 activity were observed to disappear in all IRBIT mutants in which the phosphorylation sites had been substituted with alanine (FIG. 15). This demonstrates that phosphorylation of IRBIT is required for activation of pNBC1.

INDUSTRIAL APPLICABILITY

IRBIT is involved in protein synthesis, phosphatidylinositol metabolism, or intracellular pH maintenance within mammalian cells via its binding to CPSF, PIPKII, or pNBC1. Hence, IRBIT controlling such biological functions, a nucleic acid controlling IRBIT expression and translation, or an antibody against IRBIT is useful for treating diseases arising from abnormalities in such functions. Hence, the composition and methods according to the present invention are useful for treating diseases arising from abnormalities in such functions.

According to the present invention, it is revealed that IRBIT is extremely significant in all cells for regulating intracellular metabolism, pH change, ion balance, phospholipid metabolism, control of protein synthesis, control of $Ca^{2+}$ release, and the like. Through control of the concentration or expression pattern of IRBIT, such various biological functions can be controlled. IRBIT is strongly expressed in the cerebral nervous system such as in the choroid plexus, neurons, and glial cells, and it also contributes to the control of the functions of the cerebral nervous system. Furthermore, IRBIT is useful for treating diseases that are developed when the functions of pNBC1, which are important in intracellular pH maintenance, are activated, and in particular, when pH approaches or changes to acidic levels. Examples of such diseases include eye diseases such as glaucoma and cataract and diseases such as dwarfism, mental retardation, and pancreatitis. Furthermore, IRBIT has an effect of suppressing or inhibiting PIPKII activity, so that IRBIT can be used for treating type 2 diabetes. As described above, three proteins that are targets of IRBIT were specified by the present invention. IRBIT, an inhibitor of IRBIT, and an agent for enhancing IRBIT are useful for controlling biological functions that are exerted in vivo by the target proteins.

All publications, patents, and patent applications cited herein are incorporated herein by reference in their entirety.

The invention claimed is:

1. A method for using an $IP_3$ receptor-binding protein (IRBIT) to conduct in vitro or ex vivo control of protein synthesis involved in cytoplasmic mRNA polyadenylation mediated by cleavage/polyadenylation specificity factor (CPSF) within mammalian cells, comprising:
introducing a vector capable of expressing DNA encoding IRBIT into the cells to modulate the binding of the IRBIT to the CPSF within the cells, thereby controlling the protein synthesis within the cells,
wherein the IRBIT is from a mammal; and
wherein the ex vivo control comprises removing the cells from a patient prior to the introducing step and returning the cells after the introducing step.

2. The method according to claim 1, wherein the IRBIT is a protein comprising an amino acid sequence shown in SEQ ID NO: 1 or SEQ ID NO: 3 or a protein which comprises an amino acid sequence having 98% or more identity with said amino acid sequence and has an ability to suppress the protein synthesis by binding CPSF.

3. The method of claim 1, wherein the control is in vitro control and the mammalian cell is selected from the group consisting of CHO, COS, HEK293, HeLa and NIH3T3 cells.

4. The method of claim 1, wherein the control is ex vivo control and the mammalian cell is a tumor cell.

5. The method according to claim 1, wherein the mammalian cell is a neuronal cell.

* * * * *

SEQUENCE LISTING

```
<160> NUMBER OF SEQ ID NOS: 6

<210> SEQ ID NO 1
<211> LENGTH: 530
<212> TYPE: PRT
<213> ORGANISM: Homo sapiens

<400> SEQUENCE: 1

Met Ser Met Pro Asp Ala Met Pro Leu Pro Gly Val Gly Glu Glu Leu
 1               5                  10                  15

Lys Gln Ala Lys Glu Ile Glu Asp Ala Glu Lys Tyr Ser Phe Met Ala
            20                  25                  30

Thr Val Thr Lys Ala Pro Lys Lys Gln Ile Gln Phe Ala Asp Asp Met
        35                  40                  45

Gln Glu Phe Thr Lys Phe Pro Thr Lys Thr Gly Arg Arg Ser Leu Ser
    50                  55                  60
```

```
Arg Ser Ile Ser Gln Ser Ser Thr Asp Ser Tyr Ser Ser Ala Ala Ser
 65                  70                  75                  80

Tyr Thr Asp Ser Ser Asp Asp Glu Val Ser Pro Arg Glu Lys Gln Gln
                 85                  90                  95

Thr Asn Ser Lys Gly Ser Ser Asn Phe Cys Val Lys Asn Ile Lys Gln
            100                 105                 110

Ala Glu Phe Gly Arg Arg Glu Ile Glu Ile Ala Glu Gln Asp Met Ser
        115                 120                 125

Ala Leu Ile Ser Leu Arg Lys Arg Ala Gln Gly Glu Lys Pro Leu Ala
    130                 135                 140

Gly Ala Lys Ile Val Gly Cys Thr His Ile Thr Ala Gln Thr Ala Val
145                 150                 155                 160

Leu Ile Glu Thr Leu Cys Ala Leu Gly Ala Gln Cys Arg Trp Ser Ala
                165                 170                 175

Cys Asn Ile Tyr Ser Thr Gln Asn Glu Val Ala Ala Ala Leu Ala Glu
            180                 185                 190

Ala Gly Val Ala Val Phe Ala Trp Lys Gly Glu Ser Glu Asp Asp Phe
        195                 200                 205

Trp Trp Cys Ile Asp Arg Cys Val Asn Met Asp Gly Trp Gln Ala Asn
    210                 215                 220

Met Ile Leu Asp Asp Gly Gly Asp Leu Thr His Trp Val Tyr Lys Lys
225                 230                 235                 240

Tyr Pro Asn Val Phe Lys Lys Ile Arg Gly Ile Val Glu Glu Ser Val
                245                 250                 255

Thr Gly Val His Arg Leu Tyr Gln Leu Ser Lys Ala Gly Lys Leu Cys
            260                 265                 270

Val Pro Ala Met Asn Val Asn Asp Ser Val Thr Lys Gln Lys Phe Asp
        275                 280                 285

Asn Leu Tyr Cys Cys Arg Glu Ser Ile Leu Asp Gly Leu Lys Arg Thr
    290                 295                 300

Thr Asp Val Met Phe Gly Gly Lys Gln Val Val Val Cys Gly Tyr Gly
305                 310                 315                 320

Glu Val Gly Lys Gly Cys Cys Ala Ala Leu Lys Ala Leu Gly Ala Ile
                325                 330                 335

Val Tyr Ile Thr Glu Ile Asp Pro Ile Cys Ala Leu Gln Ala Cys Met
            340                 345                 350

Asp Gly Phe Arg Val Val Lys Leu Asn Glu Val Ile Arg Gln Val Asp
        355                 360                 365

Val Val Ile Thr Cys Thr Gly Asn Lys Asn Val Val Thr Arg Glu His
370                 375                 380

Leu Asp Arg Met Lys Asn Ser Cys Ile Val Cys Asn Met Gly His Ser
385                 390                 395                 400

Asn Thr Glu Ile Asp Val Thr Ser Leu Arg Thr Pro Glu Leu Thr Trp
                405                 410                 415

Glu Arg Val Arg Ser Gln Val Asp His Val Ile Trp Pro Asp Gly Lys
            420                 425                 430

Arg Val Val Leu Leu Ala Glu Gly Arg Leu Leu Asn Leu Ser Cys Ser
        435                 440                 445

Thr Val Pro Thr Phe Val Leu Ser Ile Thr Ala Thr Thr Gln Ala Leu
    450                 455                 460

Ala Leu Ile Glu Leu Tyr Asn Ala Pro Glu Gly Arg Tyr Lys Gln Asp
465                 470                 475                 480

Val Tyr Leu Leu Pro Lys Lys Met Asp Glu Tyr Val Ala Ser Leu His
```

|       |       |       |       | 485   |       |       |       |       | 490   |       |       |       |       | 495   |
|-------|-------|-------|-------|-------|-------|-------|-------|-------|-------|-------|-------|-------|-------|-------|

Leu Pro Ser Phe Asp Ala His Leu Thr Glu Leu Thr Asp Asp Gln Ala
            500                 505                 510

Lys Tyr Leu Gly Leu Asn Lys Asn Gly Pro Phe Lys Pro Asn Tyr Tyr
        515                 520                 525

Arg Tyr
    530

<210> SEQ ID NO 2
<211> LENGTH: 2677
<212> TYPE: DNA
<213> ORGANISM: Homo sapiens

<400> SEQUENCE: 2

| cagagtgccc tttctccccg cctcttcccc ctcccgggag ctgccagtac ttgacgtggc | 60 |
| gtcaccgccc tctaccctcg ctttgcgtgc gtgtttgcgt acagcggagg tggcggcgcg | 120 |
| ggcaggtcgg agctcggagc tgctgcttct ggttctcttg tggccaccgt cgctgtccgg | 180 |
| ctgccttggg ctgccgaaca gacaaggcgt gggccacagc acctcagaag ccgacgcagc | 240 |
| tcgacgcagg ggccggcagg agggtgggcg atcgcgtgtc ggagggcgcc cgcgcgggcag | 300 |
| gcgggcgggc gccagagggg gaaagaggcg ggggcggcgg gtcagccgct ggccgggccg | 360 |
| gcggggggaat gtcgatgcct gacgcgatgc cgctgcccgg ggtcggggag gagctgaagc | 420 |
| aggccaagga gatcgaggac gccgagaagt actccttcat ggccaccgtc accaaggcgc | 480 |
| ccaagaagca aatccagttt gctgatgaca tgcaggagtt caccaaattc cccaccaaaa | 540 |
| ctggccgaag atctttgtct cgctcgatct cacagtcctc cactgacagc tacagttcag | 600 |
| ctgcatccta cacagatagc tctgatgatg aggtttctcc ccgagagaag cagcaaacca | 660 |
| actccaaggg cagcagcaat ttctgtgtga agaacatcaa gcaggcagaa tttggacgcc | 720 |
| gggagattga gattgcagag caagacatgt ctgctctgat ttcactcagg aaacgtgctc | 780 |
| agggggagaa gcccttggct ggtgctaaaa tagtgggctg tacacacatc acagcccaga | 840 |
| cagcggtgtt gattgagaca ctctgtgccc tgggggctca gtgccgctgg tctgcttgta | 900 |
| acatctactc aactcagaat gaagtagctg cagcactggc tgaggctgga gttgcagtgt | 960 |
| tcgcttggaa gggcgagtca gaagatgact tctggtggtg tattgaccgc tgtgtgaaca | 1020 |
| tggatgggtg gcaggccaac atgatcctgg atgatggggg agacttaacc cactgggttt | 1080 |
| ataagaagta tccaaacgtg tttaagaaga tccgaggcat tgtggaagag agcgtgactg | 1140 |
| gtgttcacag gctgtatcag ctctccaaag ctgggaagct ctgtgttccg gccatgaacg | 1200 |
| tcaatgattc tgttaccaaa cagaagtttg ataacttgta ctgctgccga gaatccattt | 1260 |
| tggatggcct gaagaggacc acagatgtga tgtttggtgg aaacaagtg gtggtgtgtg | 1320 |
| gctatggtga ggtaggcaag ggctgctgtg ctgctctcaa agctcttgga gcaattgtct | 1380 |
| acattaccga aatcgacccc atctgtgctc tgcaggcctg catggatggg ttcagggtgg | 1440 |
| taaagctaaa tgaagtcatc cggcaagtcg atgtcgtaat aacttgcaca ggaaataaga | 1500 |
| atgtagtgac acgggagcac ttggatcgca tgaaaaacag ttgtatcgta tgcaatatgg | 1560 |
| gccactccaa cacagaaatc gatgtgacca gcctccgcac tccggagctg acgtgggagc | 1620 |
| gagtacgttc tcaggtggac catgtcatct ggccagatgc caaacgagtt gtcctcctgg | 1680 |
| cagagggtcg tctactcaat ttgagctgct ccacagttcc caccttttgtt ctgtccatca | 1740 |
| cagccacaac acaggctttg gcactgatag aactctataa tgcacccgag gggcgataca | 1800 |
| agcaggatgt gtacttgctt cctaagaaaa tggatgaata cgttgccagc ttgcatctgc | 1860 |

```
catcatttga tgcccacctt acagagctga cagatgacca agcaaaatat ctgggactca    1920
acaaaaatgg gccattcaaa cctaattatt acagatacta atggaccata ctaccaagga    1980
ccagtccacc tgaaccacac actctaaaga aatattttt aagataactt ttatttctt     2040 cttactcctt tcctcttgat tttttcta taatttcatt cttgttttt catctcatta     2100 tccaagttct gcagaccaca caggaacttg cttcatggct cttagatga aatagaagtt    2160 cagggtccct cactctagtc actaaagaag gattttactc ccccagccca gaaggtgat    2220 tcttctcttt accatttctg gggactttag tcttaattag gtaccttatt aacaggaaat    2280
gctaaggtac cttctctgtg aacaatctg caatgtctaa atcgccttaa aagagcccat    2340
ttcttagctg ctgaaatcag tgctctttca cttcttcaga gaagcaggga tggtacctac    2400
ccggcaggta ggttagatgt gggtggtgca tgttaatttc ccttagaagt tccaagccct    2460
gtttcctgcg taaaggtggt atgtccagtt cagagatgtg tataatgagc atggcttgtt    2520
aagatcagga ggcccacttg gatttatagt atagccttc ctccactccc accagacttg    2580
ctcatttttc gagtttttaa ctagactaca ctctatttga gtttaatttt gtcctctagg    2640
atttatttct gttgtccaaa aaaaaaaaaa aaaaaaa                             2677
```

<210> SEQ ID NO 3
<211> LENGTH: 530
<212> TYPE: PRT
<213> ORGANISM: Mus musculus

<400> SEQUENCE: 3

```
Met Ser Met Pro Asp Ala Met Pro Leu Pro Gly Val Gly Glu Glu Leu
 1               5                   10                  15

Lys Gln Ala Lys Glu Ile Glu Asp Ala Glu Lys Tyr Ser Phe Met Ala
            20                  25                  30

Thr Val Thr Lys Ala Pro Lys Lys Gln Ile Gln Phe Ala Asp Asp Met
        35                  40                  45

Gln Glu Phe Thr Lys Phe Pro Thr Lys Thr Gly Arg Arg Ser Leu Ser
    50                  55                  60

Arg Ser Ile Ser Gln Ser Ser Thr Asp Ser Tyr Ser Ser Ala Ala Ser
65                  70                  75                  80

Tyr Thr Asp Ser Asp Asp Glu Val Ser Pro Arg Glu Lys Gln Gln
                85                  90                  95

Thr Asn Ser Lys Gly Ser Ser Asn Phe Cys Val Lys Asn Ile Lys Gln
            100                 105                 110

Ala Glu Phe Gly Arg Arg Glu Ile Glu Ile Ala Glu Gln Asp Met Ser
        115                 120                 125

Ala Leu Ile Ser Leu Arg Lys Arg Ala Gln Gly Glu Lys Pro Leu Ala
    130                 135                 140

Gly Ala Lys Ile Val Gly Cys Thr His Ile Thr Ala Gln Thr Ala Val
145                 150                 155                 160

Leu Ile Glu Thr Leu Cys Ala Leu Gly Ala Gln Cys Arg Trp Ser Ala
                165                 170                 175

Cys Asn Ile Tyr Ser Thr Gln Asn Glu Val Ala Ala Ala Leu Ala Glu
            180                 185                 190

Ala Gly Val Ala Val Phe Ala Trp Lys Gly Ser Glu Asp Asp Phe
        195                 200                 205

Trp Trp Cys Ile Asp Arg Cys Val Asn Met Asp Gly Trp Gln Ala Asn
    210                 215                 220

Met Ile Leu Asp Asp Gly Gly Asp Leu Thr His Trp Val Tyr Lys Lys
```

```
                225                 230                 235                 240
Tyr Pro Asn Val Phe Lys Lys Ile Arg Gly Ile Val Glu Glu Ser Val
                    245                 250                 255

Thr Gly Val His Arg Leu Tyr Gln Leu Ser Lys Ala Gly Lys Leu Cys
                260                 265                 270

Val Pro Ala Met Asn Val Asn Asp Ser Val Thr Lys Gln Lys Phe Asp
            275                 280                 285

Asn Leu Tyr Cys Cys Arg Glu Ser Ile Leu Asp Gly Leu Lys Arg Thr
        290                 295                 300

Thr Asp Val Met Phe Gly Gly Lys Gln Val Val Cys Gly Tyr Gly
305                 310                 315                 320

Glu Val Gly Lys Gly Cys Cys Ala Ala Leu Lys Ala Leu Gly Ala Ile
                325                 330                 335

Val Tyr Ile Thr Glu Ile Asp Pro Ile Cys Ala Leu Gln Ala Cys Met
                340                 345                 350

Asp Gly Phe Arg Val Val Lys Leu Asn Glu Val Ile Arg Gln Val Asp
            355                 360                 365

Val Val Ile Thr Cys Thr Gly Asn Lys Asn Val Thr Arg Glu His
        370                 375                 380

Leu Asp Arg Met Lys Asn Ser Cys Ile Val Cys Asn Met Gly His Ser
385                 390                 395                 400

Asn Thr Glu Ile Asp Val Thr Ser Leu Arg Thr Pro Glu Leu Thr Trp
                405                 410                 415

Glu Arg Val Arg Ser Gln Val Asp His Val Ile Trp Pro Asp Gly Lys
                420                 425                 430

Arg Val Val Leu Leu Ala Glu Gly Arg Leu Leu Asn Leu Ser Cys Ser
            435                 440                 445

Thr Val Pro Thr Phe Val Leu Ser Ile Thr Ala Thr Thr Gln Ala Leu
        450                 455                 460

Ala Leu Ile Glu Leu Tyr Asn Ala Pro Glu Gly Arg Tyr Lys Gln Asp
465                 470                 475                 480

Val Tyr Leu Leu Pro Lys Lys Met Asp Glu Tyr Val Ala Ser Leu His
                485                 490                 495

Leu Pro Ser Phe Asp Ala His Leu Thr Glu Leu Thr Asp Asp Gln Ala
                500                 505                 510

Lys Tyr Leu Gly Leu Asn Lys Asn Gly Pro Phe Lys Pro Asn Tyr Tyr
            515                 520                 525

Arg Tyr
    530

<210> SEQ ID NO 4
<211> LENGTH: 2427
<212> TYPE: DNA
<213> ORGANISM: Mus musculus

<400> SEQUENCE: 4
tgctgttgct tctggttctg tggccgccgt cgctgtccgg caggctccgg tctcggagcc      60
gacgaggcgc gcgagcgcgg gtcccagccc ttcggaagcc caagcagctc ggcgcggggc     120
ctggcgggaa ggcgggcgag cgcgtggccg agggcgccgc gcggacgggc gggcgcccgt     180
gagggamaga ggcgggggcg gcgggttagc cgcgggccgg gccggccggg ggatgtcgat     240
gcctgacgcg atgccgctgc ccggggtcgg ggaggagctg aaacaggcca aggagatcga     300
ggacgccgag aagtactcct tcatggccac ggtcaccaag gctcccaaga gcaaatcca     360 gtttgctgat gacatgcaag agttcaccaa attccctact aagactggcc ggagatcttt     420
```

```
gtctcgttcc atctcacaat cctccacaga cagctacagt tcagctgcat cctatacaga    480
tagctctgat gatgaggttt cccctcgaga gaagcagcaa accaactcga agggcagcag    540
caatttctgt gtgaagaaca tcaagcaggc agagtttgga cgccgggaga ttgagattgc    600
agagcaagac atgtctgctc tgatttcact caggaaacgt gctcagggag agaagccttt    660
ggctggtgct aaaatagtgg gctgtacgca catcacggcc cagacagcgg tattaattga    720
gacccttcgt gccctgggag ctcagtgccg ctggtctgcc tgcaacatct attcaactca    780
gaatgaagta gctgcagcac tggctgaggc tggagtcgcg gtgtttgctt ggaagggcga    840
gtcagaagat gatttctggt ggtgcattga ccgctgtgtc aacatggatg ggtggcaggc    900
taacatgatc ctggatgatg ggggagactt aacccactgg gtttataaga agtatccaaa    960
cgtgtttaag aagatccgag gcattgtgga agagagcgtg actggtgttc acaggctgta    1020
tcagctctcc aaagctggga agctctgtgt tccagccatg aatgtcaatg attctgttac    1080
caaacagaag tttgataacc tgtactgctg ccgagaatcc attttggatg gcctgaagag    1140
gaccacggat gtgatgtttg gtgggaaaca ggtggtggtg tgtggctatg gtgaggtagg    1200
aaagggctgc tgtgctgctc tcaaggcccc tggagcaatt gtctacataa cagaaattga    1260
ccccatctgt gctctgcagg cctgcatgga tgggttcagg gtggtgaagc tgaatgaagt    1320
catccggcag gtggacgttg taattacttg cacaggaaat aagaatgtag tgactcggga    1380
gcacttggac cgaatgaaaa atagttgtat tgtgtgcaat atgggccatt ccaacacgga    1440
gatcgacgtg accagcctcc gcactccaga actaacatgg gagcgtgtac gttctcaggt    1500
ggaccatgtc atctggcctg atggcaaacg ggtcgtcctt ctagcagagg gccgtttact    1560
taatctgagc tgctccacag tccctacctt tgttctttcc atcacggcta caacacaggc    1620
tttggcactg atagagcttt acaacgcccc ggagggacgc tacaaacagg atgtgtactt    1680
gcttcctaag aagatggatg aatatgttgc cagcttgcac ytaccatcat ttgatgccca    1740
cctgacagaa ctgacagatg accaagcaaa gtatctggga ctcaacaaaa atgggccatt    1800
caaacctaat tattacagat actaatggac atagtacagt gaccagtcca catgaaccac    1860
gcaactctaa tagagtattt tttaagataa ctttattttt cttcttatta cttttccttt    1920
gatttttttt ttctatcatt tcattgttgt tttctcatct catcatttga gttttgcaga    1980
ccacacagga acttgctcca tagctctttta ggtgaaactg aggtcaaagg tttctcaccc    2040
aagtcactaa aaggggttaa ctctgctgcc cagaaagttg attctttaac catttctggg    2100
aactttgatc gtatttagtt accttattaa cagaaaatgc taaggcatct tctatgtgga    2160
acaatctaca gtgtctaaat tgccttaaaa gagcctgttc ctagctgctg gaactagtgc    2220
tctttcactt cttcagagga gccaggatgg tacttcccag ccaggtaggt tagatgtagg    2280
tggtgcatgt cagcttccca tagacactct aagccctgtt tcctgtgtaa ggtgggyatg    2340
tctggcagag atgcgttgct tgttcaactc agtaggttca ctttgggtttg tagtccagcc    2400 ttccaccagt ctctctcatt gttctag                                       2427
```

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: siRNA

<400> SEQUENCE: 5
aaauccaguu ugcugaugac a                                             21

```
<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: siRNA

<400> SEQUENCE: 6
aacucagaau gaaguagcug c                                              21
```